(12) United States Patent
Sasso et al.

(10) Patent No.: US 8,491,634 B2
(45) Date of Patent: Jul. 23, 2013

(54) REPLACEMENT FACET JOINT AND METHOD

(76) Inventors: Ricardo C. Sasso, Indianapolis, IN (US); Kevin T Foley, Germantown, TN (US)

(*) Notice: Subject to any disclaimer, the term of this patent is extended or adjusted under 35 U.S.C. 154(b) by 1716 days.

(21) Appl. No.: 11/542,068

(22) Filed: Oct. 3, 2006

(65) Prior Publication Data

US 2007/0055245 A1 Mar. 8, 2007

Related U.S. Application Data

(63) Continuation-in-part of application No. 10/918,541, filed on Aug. 13, 2004, now Pat. No. 7,846,184.

(51) Int. Cl.
*A61B 17/70* (2006.01)

(52) U.S. Cl.
USPC .......................................................... 606/247

(58) Field of Classification Search
USPC .................................................. 606/246–249
See application file for complete search history.

(56) References Cited

U.S. PATENT DOCUMENTS

| | | | |
|---|---|---|---|
| 4,047,524 A | 9/1977 | Hall | |
| 4,502,161 A | 3/1985 | Wall | |
| 5,527,312 A | 6/1996 | Ray | |
| 5,810,822 A | 9/1998 | Mortier | |
| RE36,758 E | 6/2000 | Fitz | |
| 6,113,637 A | 9/2000 | Gill et al. | |
| 6,132,464 A | 10/2000 | Martin | |
| 6,280,442 B1 | 8/2001 | Barker et al. | |
| 6,419,703 B1 | 7/2002 | Fallin et al. | |
| 6,485,491 B1 | 11/2002 | Farris et al. | |
| 6,485,518 B1 | 11/2002 | Cornwall et al. | |
| 6,565,605 B2 | 5/2003 | Goble et al. | |
| 6,579,319 B2 | 6/2003 | Goble et al. | |
| 6,610,091 B1 | 8/2003 | Reiley | |
| 2002/0123806 A1 | 9/2002 | Reiley | |
| 2003/0004572 A1 | 1/2003 | Goble et al. | |
| 2003/0028250 A1 | 2/2003 | Reiley et al. | |
| 2003/0171750 A1 | 9/2003 | Chin | |
| 2005/0159746 A1 | 7/2005 | Grob et al. | |

*Primary Examiner* — Mary Hoffman

(74) *Attorney, Agent, or Firm* — Woodard, Emhardt, Moriarty, McNett & Henry LLP

(57) ABSTRACT

Prostheses and methods for repair of cervical fact joints. In one aspect, the articulating surfaces of the natural facets of a facet joint are removed only a sufficient amount to allow the insertion of flat or slightly curvilinear portions of protheses therebetween in an overlapping relationship. The portions are so inserted and the prostheses mounted by attachment to adjacent vertebrae. Also, a single natural facet may be similarly repaired with a single prosthesis. In another aspect, the invention provides a single prosthesis that is useful in repairing articulating surfaces in more than one cervical facet joint.

19 Claims, 17 Drawing Sheets

REPLACEMENT FACET JOINT AND METHOD

STATEMENT OF RELATED APPLICATIONS

This application is a continuation-in-part of U.S. patent application Ser. No. 10/918,541 filed Aug. 13, 2004, which is incorporated herein by reference in its entirety.

BACKGROUND OF THE INVENTION

1. Field of the Invention

This invention relates to methods and apparatuses for replacing and/or repairing spinal facet joints particularly in the cervical spine.

2. Description of the Prior Art

Various devices and methods have been proposed for replacing the facet joints of the spine. For example, the Fitz U.S. Pat. No. RE36,758 discloses an artificial facet joint which includes a superior component that is conical or pyramidical in form and articulates with an inferior component that is also roughly conical or pyramidical in form. The Goble et al., U.S. Pat. No. 6,579,319 discloses a prosthesis for the replacement of a vertebral facet joint which does not require attachment to or abutment against the posterior arch. The Reiley U.S. Pat. No. 6,610,091 discloses facet arthroplasty devices that provide articulating movement between superior and inferior prostheses. It is desirable that improved prostheses and methods be provided for replacement of the facet joints particularly in the cervical spine and particularly in the facet joints of C3 through C7.

One of the surgical operations performed on the spine involves the replacement of one or more intervertebral discs with a disc prosthesis. One of the problems involved in disc replacement is the restoration of spine alignment. It is desirable that improved methods and prostheses be made available for the restoration of spine alignment in various spinal surgeries, including those involving disc replacement.

SUMMARY OF THE INVENTION

One embodiment of the invention might involve a prosthesis for the repair of cervical facet joint which includes a superior component having a first flat or slightly curvilinear portion and a mounting portion. Also provided is an inferior component having a second flat or slightly curvilinear portion and a mounting portion. The mounting portions are adapted for connection to adjacent cervical vertebrae with the first and second portions articulating with each other between the facets of the adjacent cervical vertebrae.

Another embodiment of the invention might involve a prosthesis for the repair of a cervical facet joint. There is provided a component having a flat or slightly curvilinear portion and a mounting portion with the flat or slightly curvilinear portion being adapted for replacing the articulating surface of one of the facets of the articulating facet joint between the two adjacent cervical vertebrae.

Still another embodiment of the invention might include a method for repairing a cervical facet joint of adjacent vertebrae. A superior component is provided having a first flat or slightly curvilinear portion and a superior mounting portion. Also provided is an inferior component having a second flat or slightly curvilinear portion and an inferior mounting portion. The articulating surfaces of the facets are removed only a sufficient amount to allow the insertion of the first and second portions therebetween in an overlapping relationship. A further step involves inserting the first and second portions between the facets with the first and second portions in an overlapping relationship. Further, the components are secured to the adjacent vertebrae by attaching the mounting portions to the posterior arches of the adjacent vertebrae.

Still another method forming an embodiment of this invention involves repairing a cervical facet joint between a first vertebra and a second vertebra by providing a component having a first flat or slightly curvilinear portion and a mounting portion. The natural facet surface of the first vertebra is removed only a sufficient amount to allow the insertion of the first portion into overlapping relationship with the natural facet surface of the second vertebra. The first portion is inserted into overlapping relationship with the natural facet surface of the second vertebra and the component is secured to the first vertebra by attaching the mounting portion to the posterior arch of the first vertebra.

In another embodiment, the present invention provides a prosthesis for the repair of a first cervical facet joint and a second cervical facet joint occurring on a first side of a spinal column, wherein the first cervical facet joint and the second cervical facet joint each have a superior facet articulating surface and an inferior facet articulating surface. This prosthesis is comprised of a prosthetic component including a superior portion, an inferior portion, and a mounting portion. The superior portion is adapted for replacing at least a portion of the articulating surface of the first cervical facet joint superior facet, while the inferior portion is adapted for replacing at least a portion of the articulating surface of the second cervical facet joint inferior facet. The mounting portion is adapted for connection to a vertebral portion occurring between the first cervical facet joint and the second cervical facet joint. In some embodiments, the prosthesis includes a second prosthetic component comprised of an inferior portion adapted for replacing at least a portion of the articulating surface of the first cervical facet joint inferior facet, and a mounting portion adapted for connection to a vertebral portion occurring above the first cervical facet joint. Additionally or alternatively, the prosthesis may include a third prosthetic component comprised of a superior portion adapted for replacing at least a portion of the articulating surface of the second cervical facet joint superior facet, and a mounting portion adapted for connection to a vertebral portion occurring below the second cervical facet joint.

In yet another embodiment, the present invention provides a prosthesis for the repair of a first cervical facet joint and a second cervical facet joint such as those described directly above. This prosthesis includes a prosthetic component which is comprised of a superior portion and an inferior portion. The superior portion is adapted for replacing at least a portion of the articulating surface of the first cervical facet joint superior facet, while the inferior portion is adapted for replacing at least a portion of the articulating surface of the second cervical facet joint inferior facet. The prosthetic component also includes an adjustable mounting portion extending between the superior portion and the inferior portion. The mounting portion is adapted for connection to a vertebral portion occurring between the first cervical facet joint and the second cervical facet joint, and is configured for adjusting the distance between a point on the superior portion and a point on the inferior portion.

In a further embodiment, the invention provides a prosthesis for the repair of a cervical facet joint. This prosthesis comprises a component including a substantially flat or slightly curvilinear portion, a mounting portion, and an adjustable joining portion. The substantially flat or slightly curvilinear portion is adapted for replacing the articulating surface of one of the facets of the articulating facet joint between two adjacent cervical vertebrae. The joining portion joins the mounting portion to the substantially flat or slightly curvilinear portion, and is configured for adjusting the angle between the mounting portion and the substantially flat or slightly curvilinear portion. In some forms, a prosthesis is configured so that the angle between the mounting portion and the substantially flat or slightly curvilinear portion can be adjusted between about 130° and about 140°, while in other forms, between about 40° and about 50°.

In an additional embodiment, the invention provides a prosthesis for the repair of a first cervical facet joint and a second cervical facet joint such as those described above. This prosthesis is comprised of a prosthetic component including a superior portion adapted for replacing at least a portion of the articulating surface of the first cervical facet joint superior facet, an inferior portion adapted for replacing at least a portion of the articulating surface of the second cervical facet joint inferior facet, and a mounting portion adapted for connection to a vertebral portion occurring between the first cervical facet joint and the second cervical facet joint. This prosthesis also includes a first adjustable joining portion joining the superior portion to the mounting portion, and a second adjustable joining portion joining the inferior portion to the mounting portion. The first joining portion is configured for adjusting the angle between the superior portion and the mounting portion, while the second joining portion is configured for adjusting the angle between the inferior portion and the mounting portion.

Other objects, embodiments, forms, features, advantages, aspects, and benefits of the present invention shall become apparent from the detailed description and drawings included herein.

DETAILED DESCRIPTION

Figure 1:
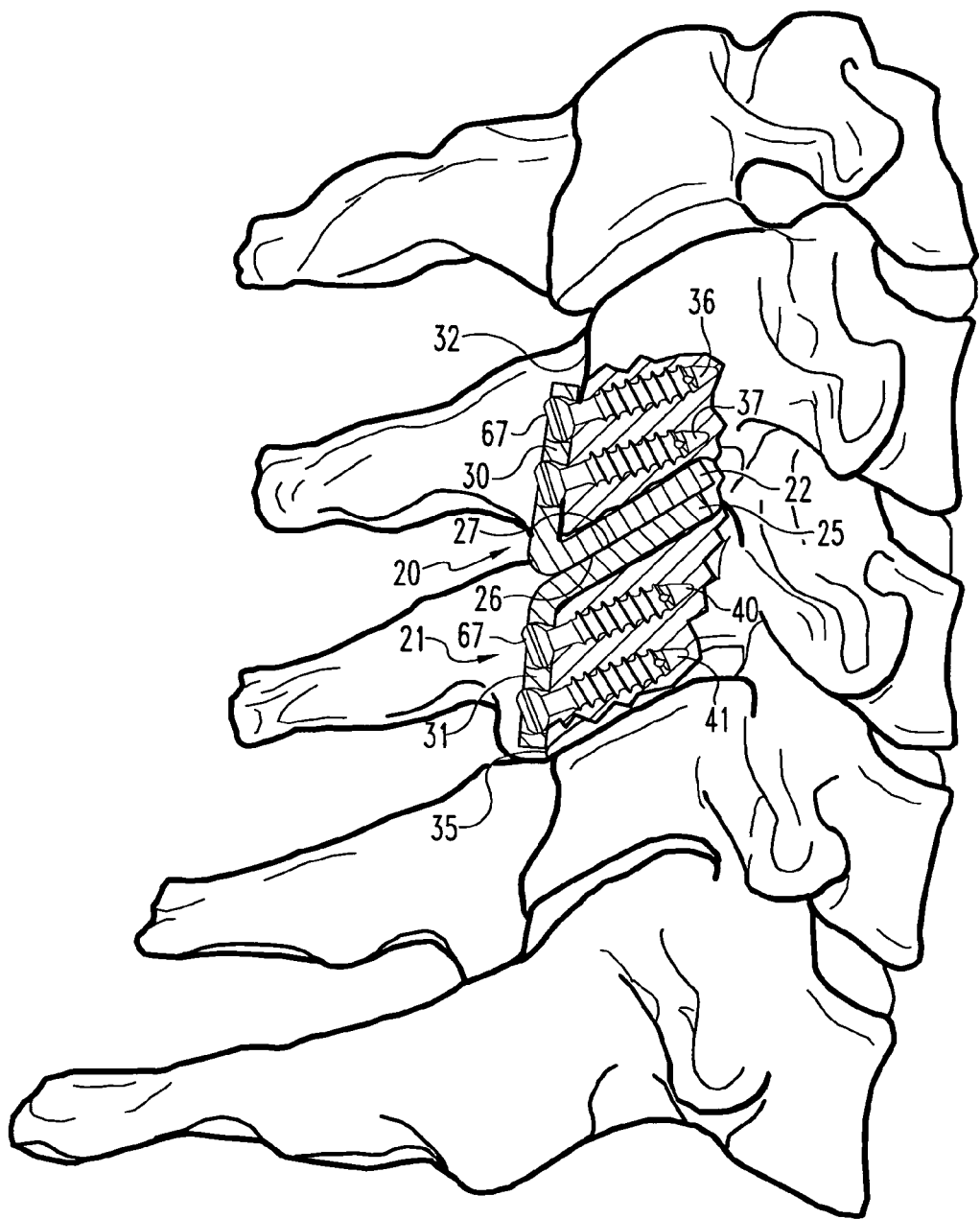
FIG. 1 is a lateral or side view of the human cervical spine with portions broken away showing one embodiment of the invention.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

The invention generally relates to artificial facet joints that are particularly configured for use in association with the cervical region of the spine. One artificial facet joint preferably includes superior and inferior components that cooperate with one another to substantially mimic normal physiological movement between the adjacent vertebrae. Implantation of this artificial facet joint does not necessarily require the removal of significant portions of the natural facet joint. Instead, the superior and inferior components are preferably configured to replace only the articulating surface portions of the natural facet joint, with the remainder of the natural facet joint remaining intact. The invention also provides, in certain embodiments, prosthetic components configured for repairing and/or replacing articulating surfaces in more than one facet joint. One illustrative component has a superior portion and an inferior portion adapted to replace at least a portion of the articulating surfaces of a superior facet and an inferior facet, respectively, occurring on the same side of a vertebra. In some forms, such a component can be combined with superior and inferior components such as those described directly above to provide a prosthesis that is suitable for replacing two facet joints occurring on the same side of a spinal column. Moreover, these artificial facet joints or other facet components do not have to constitute interbody-type devices, but might instead be mounted outside of the intervertebral disc space. Additionally, such artificial facet joints may be used in association with uni-lateral or bi-lateral treatment of the cervical spine.

Referring to FIG. 1, in one embodiment, the superior component 20 and inferior component 21 each preferably include a substantially flat or slightly curvilinear articulation portion 22 and 25, respectively, defining articulating surfaces, and a mounting flange portion 30 and 31, respectively, extending transversely from the articulation portion for posterior attachment to the lateral mass 32 and 35 of respective vertebra via one or more bone screws 36, 37, 40 and 41. The articulation and mounting portions of the superior/inferior components preferably have a relatively thin, plate-like configuration. The mating articulating surfaces of the superior and inferior components of the artificial facet joint preferably are substantially planar or flat or slightly curvilinear as opposed to defining a ball-and-socket configuration. Some slight curvature in the mating articulating surfaces, while less preferred, is contemplated as within the scope of the invention. It being understood that in embodiments having both superior and inferior components, such very slight curvature is preferably matched between the two components and that such curvature may limit the extent of articulation possible. In this manner, the interface between the superior and inferior articulation portions can be described as having a "shingle" overlap arrangement.

With regard to the superior prosthetic component 20, the angle between the articulation portion 22 and the mounting flange portion 30 is preferably about 45 degrees to approximate the angular orientation of the natural inferior articular facet relative to the posterior lateral mass. Similarly, the inferior prosthetic component 21 preferably defines an angle between the articulation and mounting portions of about 135 degrees to approximate the angular orientation of the natural superior articular facet relative to the posterior lateral mass. It should be understood that the superior and inferior components of the artificial facet joint can be formed of all materials known to those of ordinary skill in the art as being suitable for this purpose. Such materials include, but are not limited to, metal, a polymer, a ceramic, or any combination thereof. It should further be understood that it is contemplated as within the scope of the invention that portions of each component might be made of one material, and other portions of a different material and/or that portions of the component might be coated with additional materials, particularly the mounting portions that might be subject to greater wear as opposing surfaces rub against one another.

Figure 2:
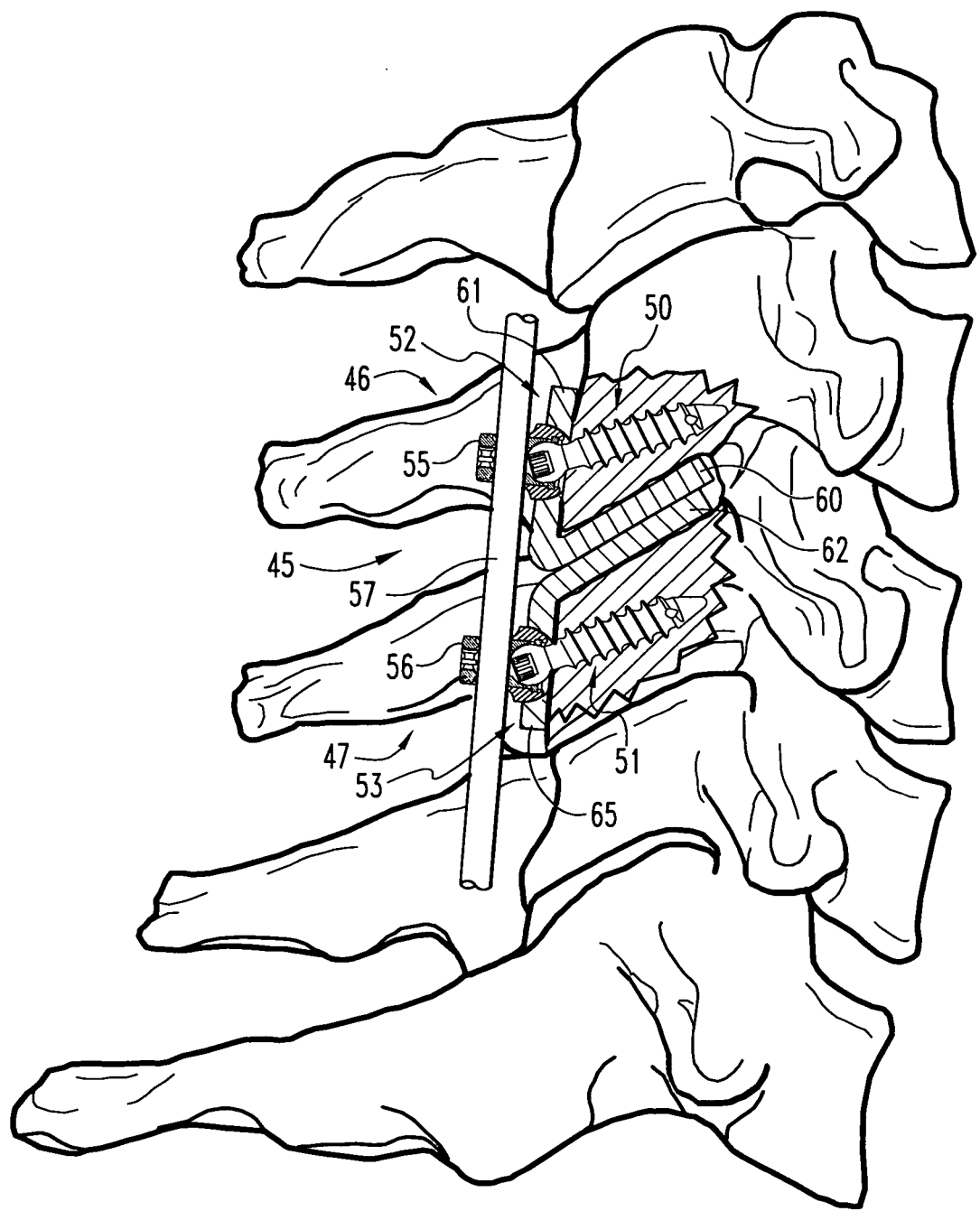
FIG. 2 is a view similar to FIG. 1 showing a further embodiment of the invention.

Referring to FIG. 2, in a further aspect of the invention, a flexible tethering system 45 is attached between, for example, the cervical vertebrae 46 and 47 to provide for flexible stabilization of the portion of the cervical spine being treated. In one embodiment, the flexible tethering system 45 might preferably include two Vertex-type screws 50 and 51 that are used to anchor the superior component 52 and inferior component 53 of the artificial facet joint to the upper and lower vertebrae, respectively. The screws 50 and 51 include receiver portions 55 and 56, respectively, that each preferably define a U-shaped channel for receiving a flexible tether 57. Flexible tether 57 is preferably a flexible rope, cable or rod. It should be understood that other types and configurations of flexible tethering systems are contemplated as within the scope of the present invention. The tethering system may be constructed and include the multi-axial bone screw assembly described and illustrated in detail in U.S. Pat. No. 6,280,442 to Barker et al. which is incorporated by reference herein. For use in the present invention, the tether 57 is preferably flexible rather than being rigid as might be required for applications in which a fixed relationship between components is desired.

Figure 3:
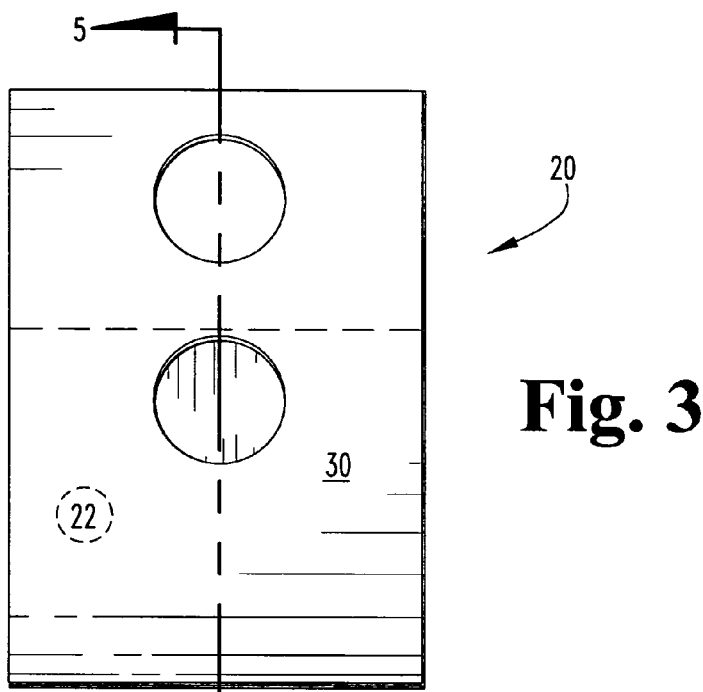
FIG. 3 is a front elevation of a superior component forming part of FIG. 1.
Figure 4:
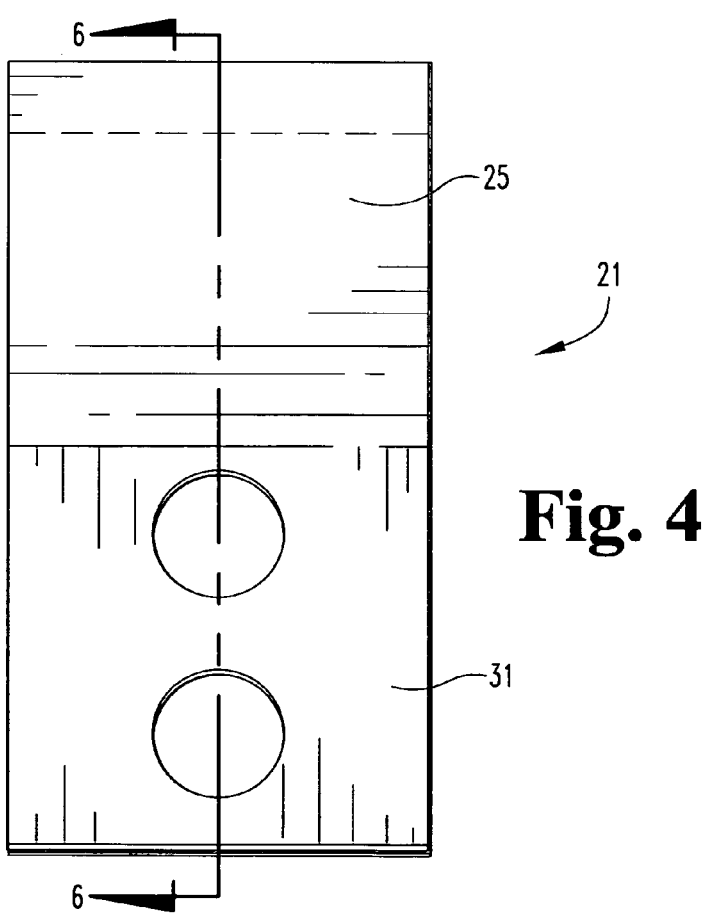
FIG. 4 is a front elevation of an inferior component forming part of FIG. 1.
Figure 5:
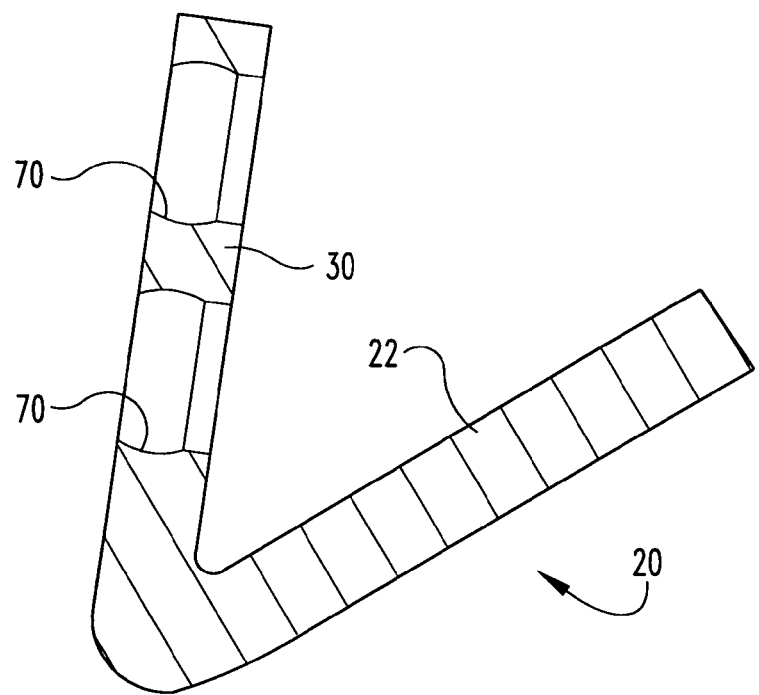
FIG. 5 is a sectional view taken in the direction of the arrows 5-5 in FIG. 3.
Figure 6:
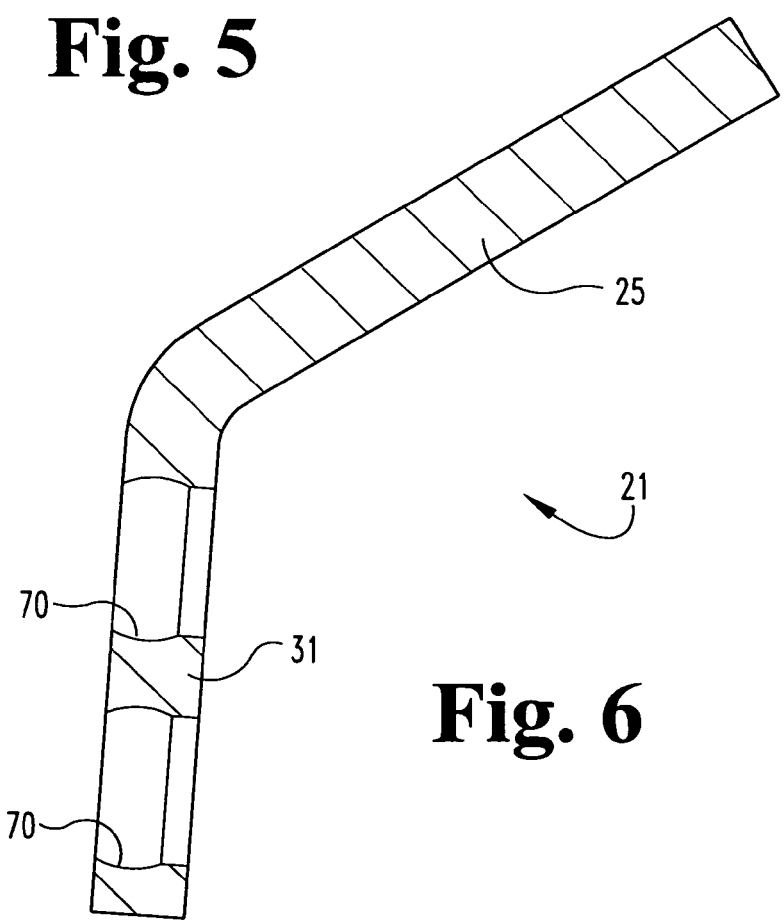
FIG. 6 is a sectional view taken in the direction of the arrows 6-6 in FIG. 4.

FIG. 3 is a front elevation and FIG. 5 is a section showing the configuration of the superior component 20. In one specific embodiment, the flat or slightly curvilinear articulation portion 22 and the mounting flange portion 30 are preferably arranged at an angle of 45° relative to one another. Alternatively, the angular relationship may be about 45°. FIG. 4 is a front elevation and FIG. 6 is a section showing the configuration of the inferior component 21. In one specific embodiment, the flat or slightly curvilinear articulation portion 25 and the mounting flange portion 31 are preferably arranged at an angle of 135° relative to one another. Alternatively, the angular relationship may be about 135°. The embodiments of FIGS. 1 and 2 are shown, respectively, with two screws per component and one screw per component although the number of screws in each embodiment may vary. Thus, the embodiment of FIG. 1 may use one screw per component and the embodiment of FIG. 2 may use two screws per component. It should be understood that it is contemplated as within the scope of the invention that each component may have a different number of anchors and that the number of anchors might be one, two or more than two anchors for each component.

Figure 7:
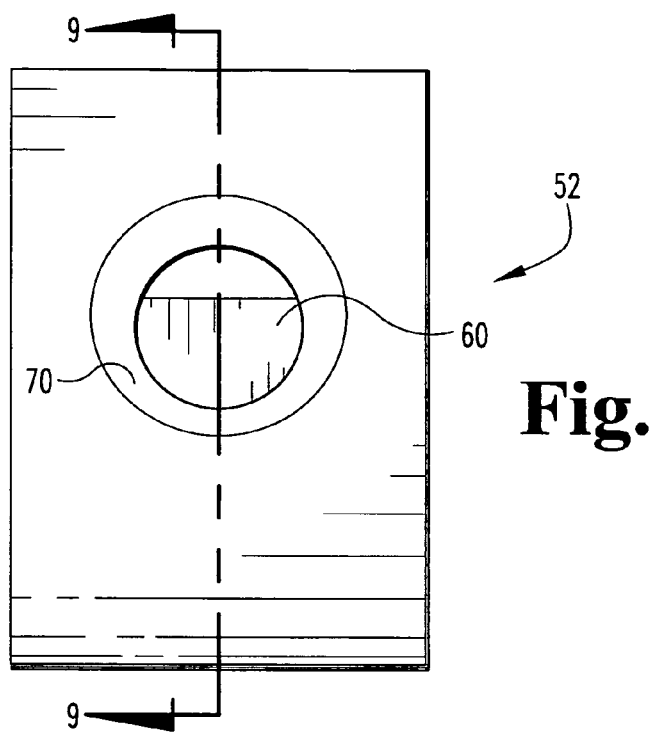
FIG. 7 is a front elevation of a superior component forming part of FIG. 2.
Figure 8:
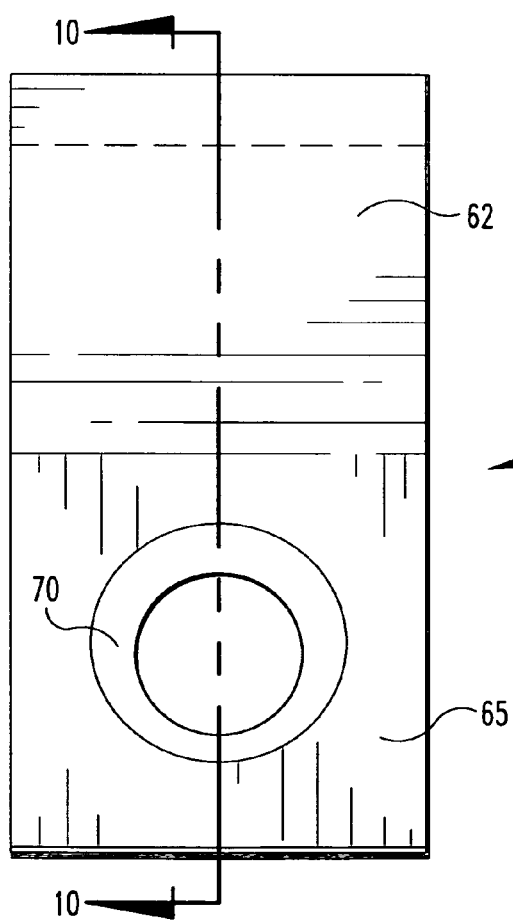
FIG. 8 is a front elevation of an inferior component forming part of FIG. 2.
Figure 9:
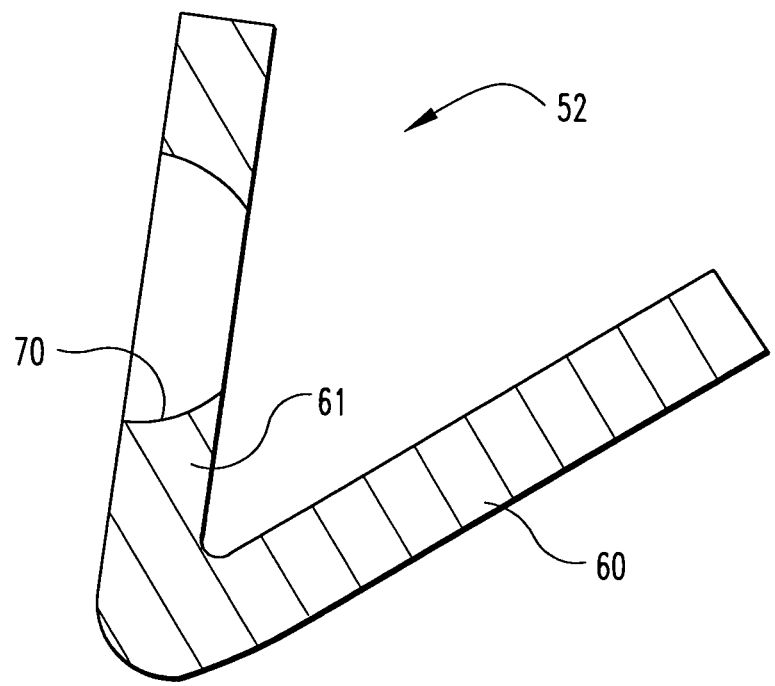
FIG. 9 is a sectional view taken in the direction of the arrows 9-9 in FIG. 7.
Figure 10:
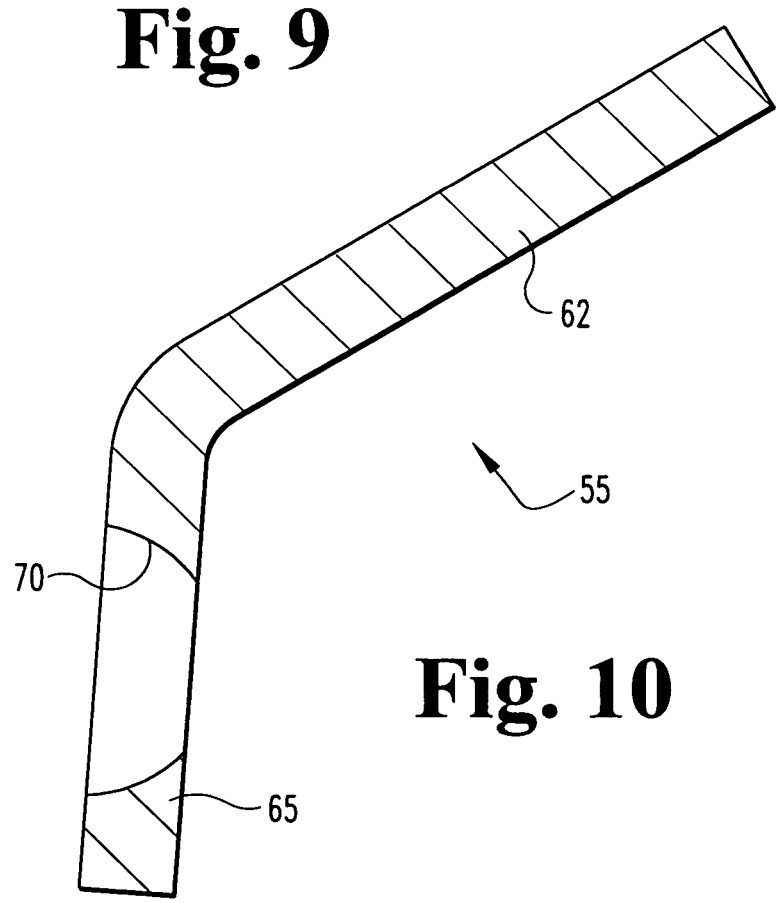
FIG. 10 is a sectional view taken in the direction of the arrows 10-10 in FIG. 8.

FIG. 7 is a front elevation and FIG. 9 is a section showing the configuration of the superior component 52. In one specific embodiment the flat or slightly curvilinear articulation portion 60 and the mounting flange portion 61 are preferably arranged at an angle of 45° relative to one another. Alternatively, the angular relationship may be about 45°. FIG. 8 is a front elevation and FIG. 10 is a section showing the configuration of the inferior component 55. In one specific embodiment, the flat or slightly curvilinear articulation portion 62 and the mounting flange portion 65 are preferably arranged at an angle of 135° relative to one another. Alternatively, the angular relationship may be about 135°.

The embodiments of FIGS. 1 and 2 are both preferably provided with mounting capabilities that allow the screw (or any other bone anchor that might be used) to attach the component to extend in the direction desired by the physician installing the component. Referring, for example, to FIG. 1, the bone screws 36, 37, 40 and 41 each preferably have rounded heads 67 that rest in rounded holes 70 (FIGS. 5 and 6) in the mounting flange portions 30 and 31. This configuration allows the surgeon to orient the screw at a variety of angles so as to place the screw in the strongest portion of the bone. This capability is also true of the multi-axial bone screw assembly of FIG. 2 as described in detail in the Barker, U.S. Pat. No. 6,280,442. Thus, the bone screw holes 70 of FIGS. 7-10 are also preferably rounded to receive the heads of their respective bone screws at a range of angles.

Figure 11:
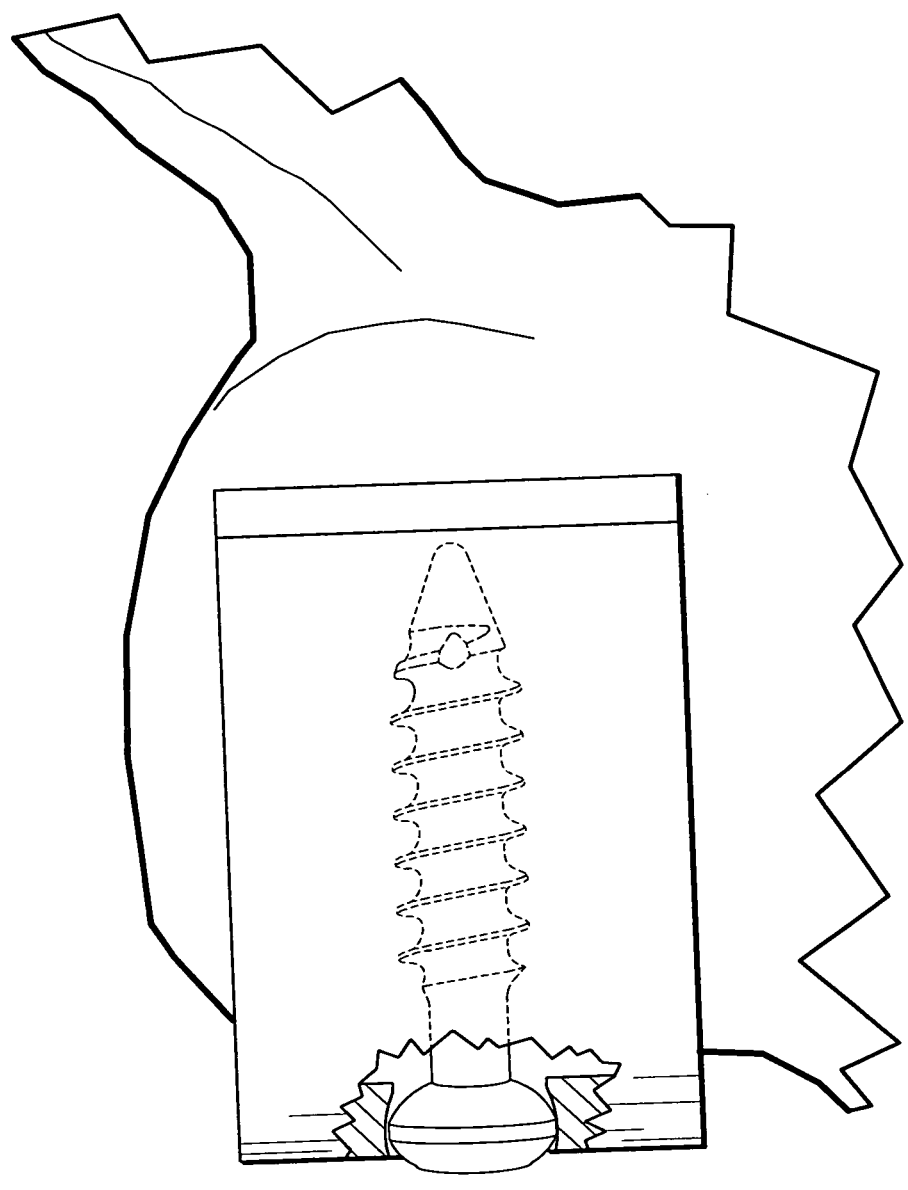
FIG. 11 is a view looking down on the facet of a cervical vertebra showing an alternative embodiment of the invention.
Figure 12:
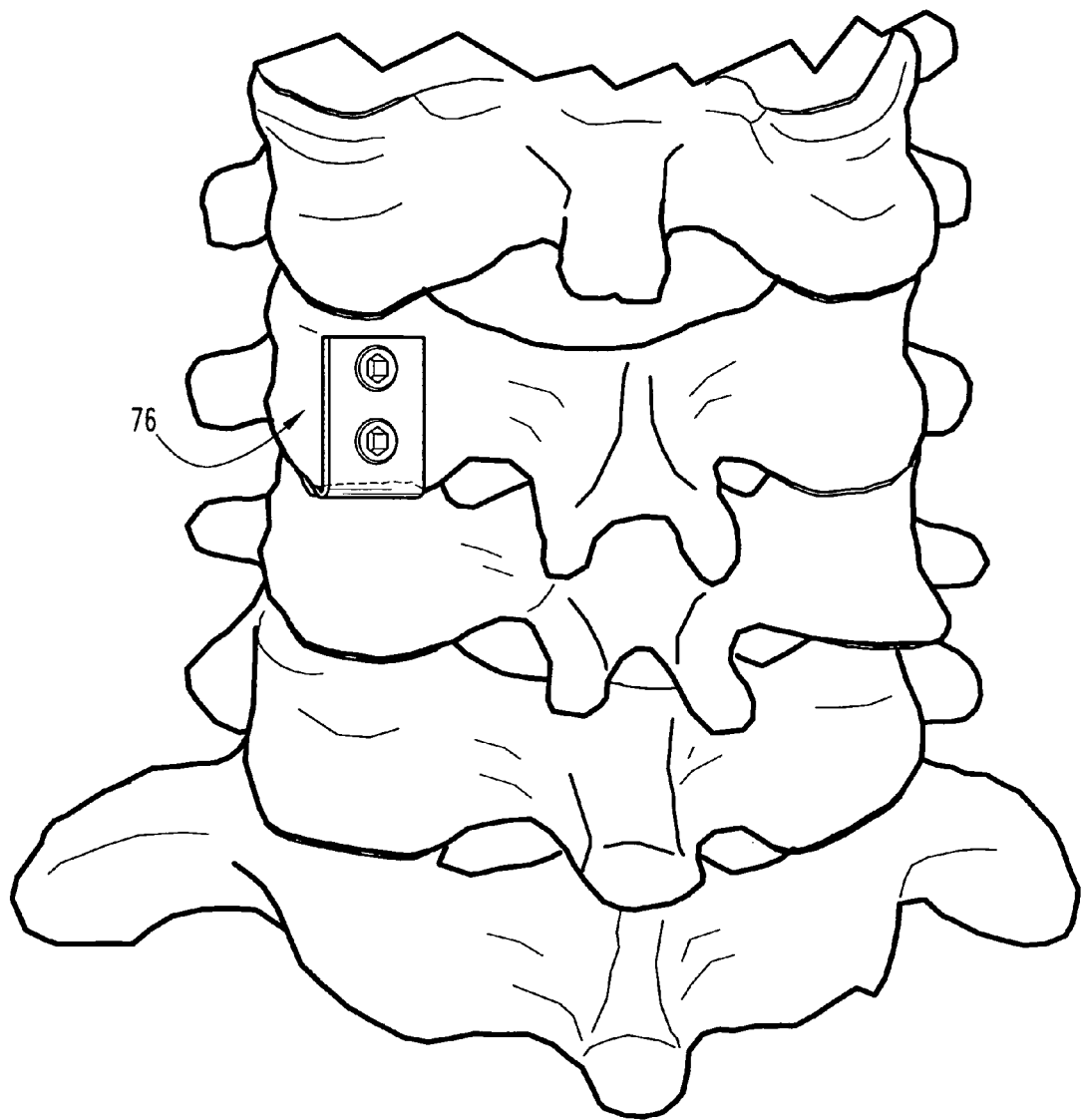
FIG. 12 is a posterior view of the cervical spine showing still another embodiment of the invention.

In certain applications, such as for example a spinal fracture, it may be appropriate to repair a cervical facet joint by replacing only one of the articulating surfaces of the natural facet joint. Thus, FIG. 11 shows a prosthesis 75 for accomplishing this purpose wherein the inferior portion of the facet joint has been replaced by the prosthesis 75 which is preferably constructed identically to the structure illustrated in FIGS. 8 and 10. FIG. 12 is a posterior view of the cervical spine and wherein the superior portion of the facet joint has been replaced by the prosthesis 76 which may preferably be constructed identically to the structure illustrated in FIGS. 3 and 5. It should be understood, however, that one or more bone screws may be used in the embodiment of FIGS. 11 and 12. Also in connection with the embodiment of FIGS. 11 and 12, it is important that the surface of the artificial articulating portion such as the surface of the portion 62 which contacts the natural facet should be made out of cartilage or biologic tissue and not be a material which causes wear on the natural facet tissue.

Figure 13:
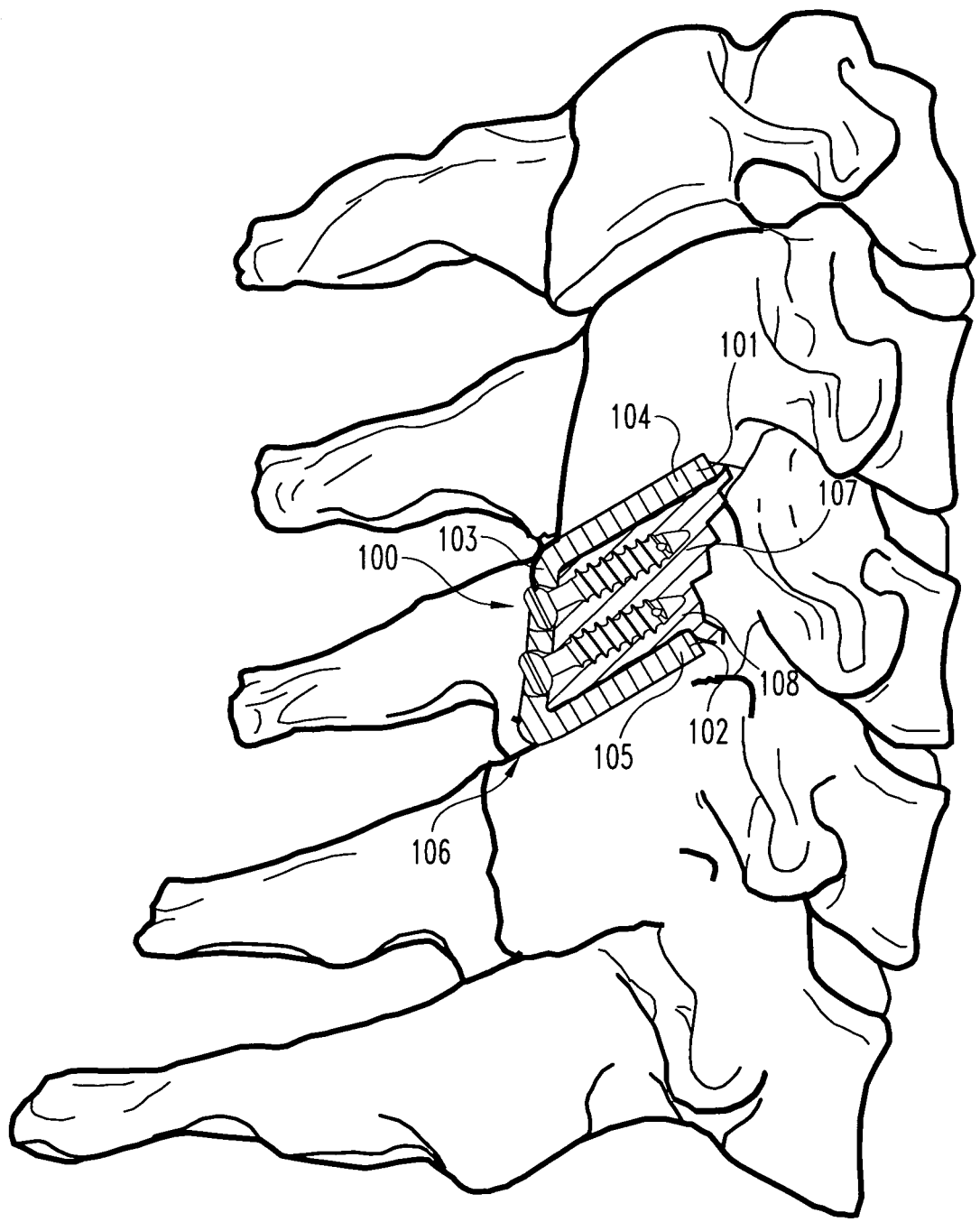
FIG. 13 is a view similar to FIG. 1 showing a further embodiment of the invention.

In some embodiments, the present invention provides prosthetic components that can be used in repairing and/or replacing articulating surfaces in two adjacent facet joints, for example, a superior facet articulating surface and an inferior facet articulating surface occurring on the same side of a cervical vertebra, and in this regard, may be considered "multilevel" facet joint treatment devices. With reference now to FIG. 13, shown is a prosthetic component 100 comprised of a superior portion 101, an inferior portion 102 and a mounting portion 103. Superior portion 101 is adapted for replacing at least a portion of the articulating surface of a superior articular facet occurring on one side of a cervical vertebra, while inferior portion 102 is adapted for replacing at least a portion of the articulating surface of the inferior articular facet occurring on this same cervical vertebra side. Superior portion 101 and inferior portion 102 include articulation portions 104 and 105, respectively, defining articulating surfaces. Superior portion 101 and inferior portion 102 extend from mounting portion 103, which is adapted for connection to the cervical vertebra, e.g., for posterior attachment to the lateral mass 106 of a vertebra via one or more bone anchor members such as bone screws 107 and 108.

It should be understood, however, that one or more bone screws or other anchoring members may be used in the embodiment of FIG. 13. Also in connection with the embodiment of FIG. 13, it is important that the surface of the artificial articulating portions such as the surface of the articulation portions 104 and 105 which contact the natural facets should be made out of cartilage or biologic tissue and not be a material which causes wear on the natural facet tissue.

The superior/inferior portions and mounting portion of prosthetic component 100 preferably have a relatively thin, plate-like configuration. The articulating surfaces of the superior and inferior portions of prosthetic component 100 preferably are substantially planar or flat or slightly curvilinear as opposed to defining a ball-and-socket configuration. Some slight curvature in the articulating surfaces, while less preferred, is contemplated as within the scope of the invention. It being understood that in embodiments including additional prosthetic components for mating with one or both articulating surfaces of the present component (for example, as described below), such very slight curvature is preferably matched between two mating surfaces and that such curvature may limit the extent of articulation possible.

The angle between the superior portion 101 and the mounting flange portion 103 is preferably 135 degrees or about 135 degrees to approximate the angular orientation of the natural superior articular facet relative to the posterior lateral mass. Similarly, the angle between the inferior portion 102 and the mounting flange portion 103 is preferably 45 degrees or thereabout to approximate the angular orientation of the natural inferior articular facet relative to the posterior lateral mass. It should be understood that prosthetic component 100, or any portion thereof, can be formed of all materials known to those of ordinary skill in the art as being suitable for this purpose. Such materials include, but are not limited to, metal, a polymer, a ceramic, or any combination thereof. In this regard, it should further be understood that it is contemplated as within the scope of the invention that a portion of prosthetic component 100 might be made of one or more of the same materials as another portion, and/or that portions of the component might be coated with additional materials, particularly the mounting portion 103 that might be subject to greater wear as the articulating surfaces rub against other surfaces.

Figure 14:
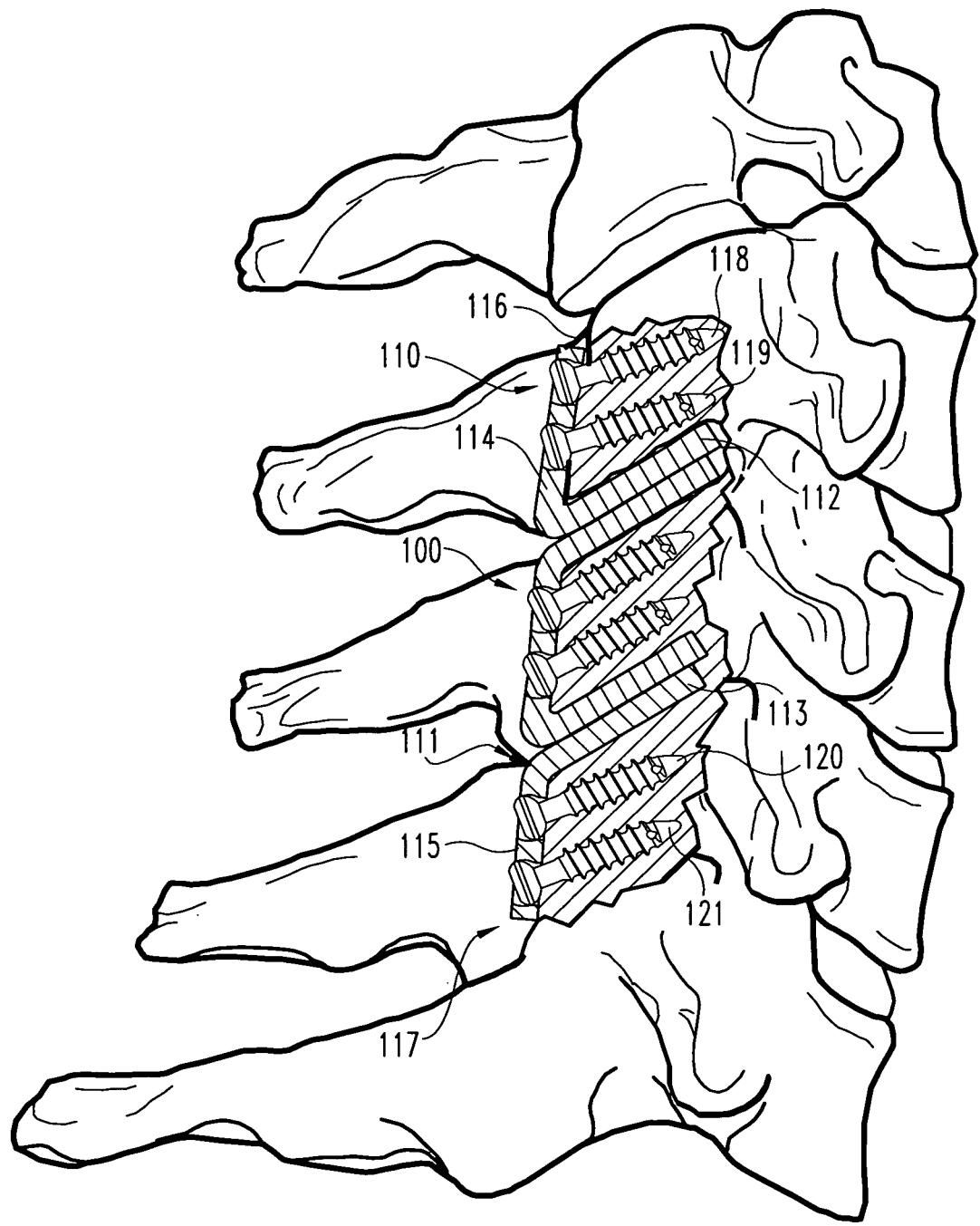
FIG. 14 is a view similar to FIG. 13 showing another embodiment of the invention.
Figure 15:
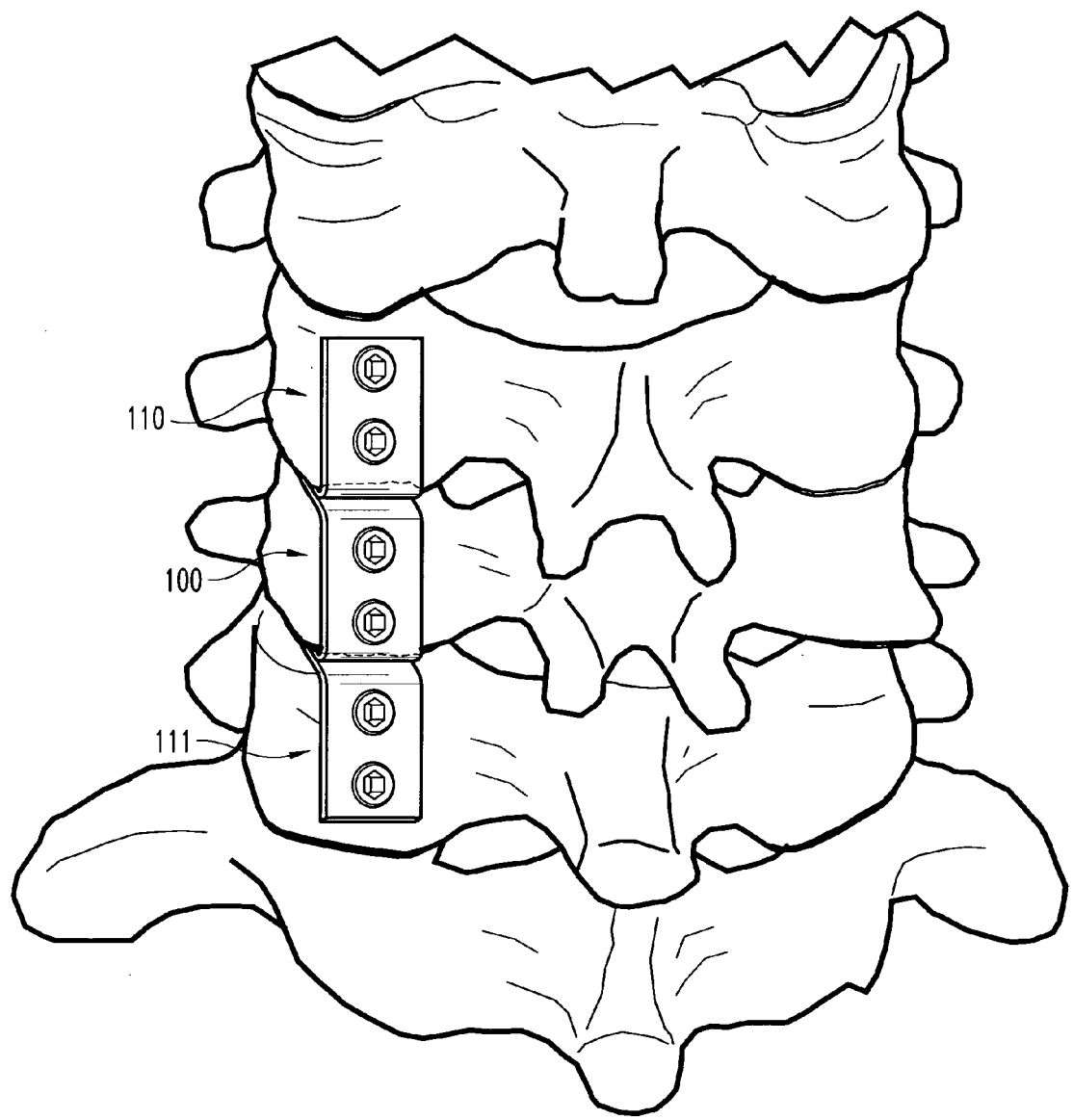
FIG. 15 is a posterior view of the cervical spine showing the embodiment out of FIG. 14.

Prosthetic component 100 can be used alone, or alternatively, can be used in conjunction with one or more other prosthetic components. For example and as illustrated in FIGS. 14 and 15, prosthetic component 100 can be combined and used with a superior prosthetic component 110 and an inferior prosthetic component 111.

Superior component 110 and inferior component 111 each preferably include a substantially flat or slightly curvilinear articulation portion 112 and 113, respectively, defining articulating surfaces, and a mounting flange portion 114 and 115, respectively, extending transversely from the articulation portion for posterior attachment to the lateral mass 116 and 117 of respective vertebra via one or more bone anchor members such as bone screws 118, 119, 120 and 121. The articulation portions of the superior/inferior components preferably have a relatively thin, plate-like configuration.

In mating with the articulating surfaces of prosthetic component 100 (hereinafter referred to as the "middle" component), the articulation surfaces of superior component 110 and inferior component 111 preferably are substantially planar or flat or slightly curvilinear as opposed to defining a ball-and-socket configuration. Some slight curvature in the mating articulating surfaces, while less preferred, is contemplated as within the scope of the invention. In this manner, such an interface between prosthetic articulation portions can be described as having a "shingle" overlap arrangement.

With regard to the superior prosthetic component 110, the angle between the articulation portion 112 and the mounting flange portion 114 is preferably 45 degrees or thereabout to approximate the angular orientation of the natural inferior articular facet relative to the posterior lateral mass. Similarly, the inferior prosthetic component 111 preferably defines an angle between the articulation and mounting portions of 135 degrees or thereabout to approximate the angular orientation of the natural superior articular facet relative to the posterior lateral mass. It should be understood that the superior and inferior components, or any portions thereof, can be comprised of all materials known to those of ordinary skill in the art as described above.

FIG. 15 is a posterior view of the cervical spine and wherein neighboring facet joints on one side of the spine have been replaced by a combination of middle component 100, superior component 110 and inferior component 111. It should be understood, however, that one or more bone screws or other suitable anchoring members may be used in the embodiments of FIGS. 13, 14 and 15. Further, any of the components may be provided with mounting capabilities that allow the screws (or any other bone anchor members that might be used to attach the component) to extend in the direction desired by the physician installing the component, for example, as described above. It will also be understood that a flexible tethering system such as that described above for FIG. 2 can be attached between or among components (whichever the case may be) in a multiple-component embodiment of the invention.

Figure 16:
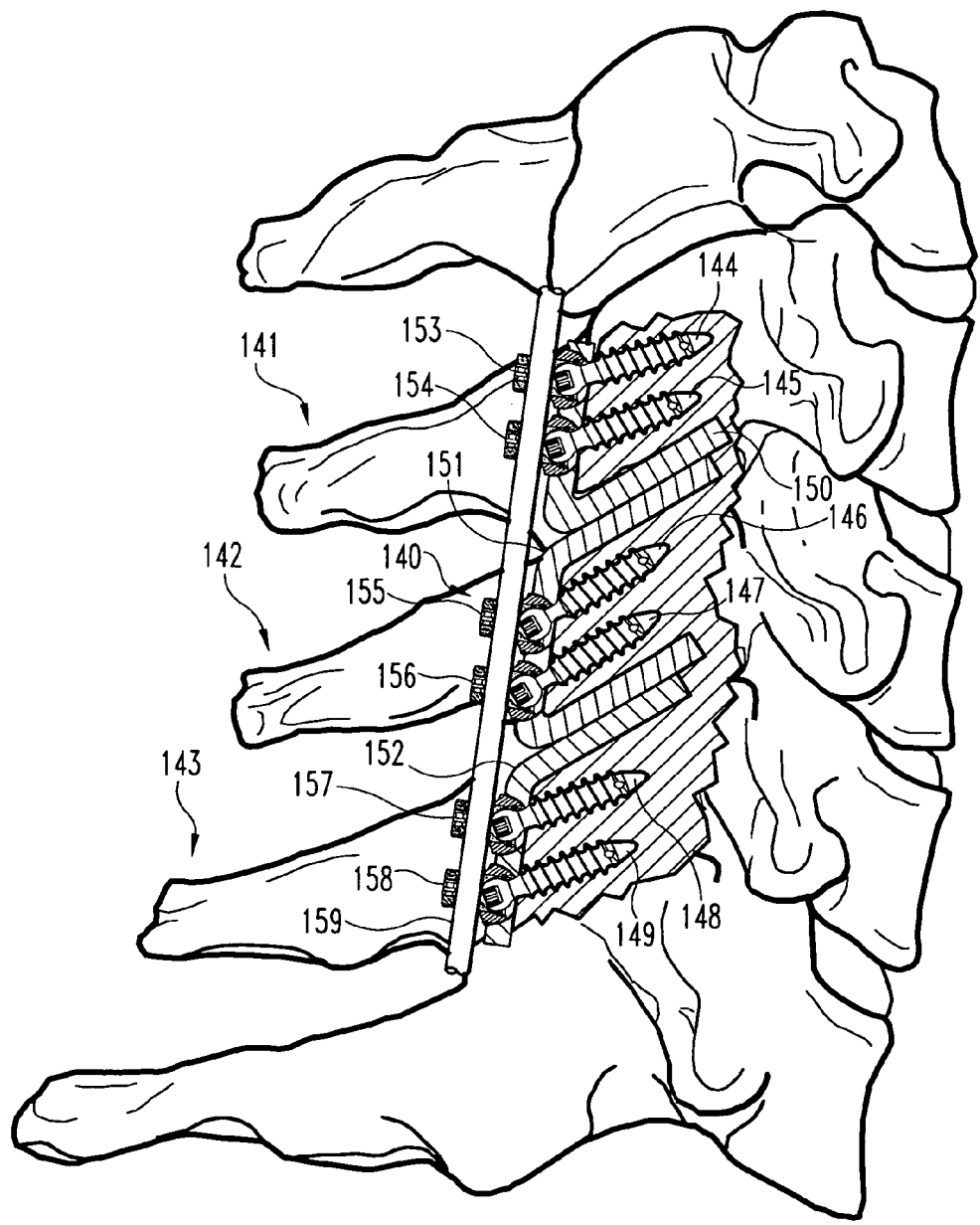
FIG. 16 is a view similar to FIG. 13 showing another embodiment of the invention.

Thus, with reference now to FIG. 16, shown is another embodiment of the invention, wherein a flexible tethering system 140 is attached among, for example, three cervical vertebrae 141, 142 and 143 to provide for flexible stabilization of the portion of the cervical spine being treated. In one embodiment, the flexible tethering system 140 might preferably include three sets of Vertex-type screws 144 and 145; 146 and 147; and 148 and 149 that are used to anchor a superior component 150, middle component 151 and inferior component 152 of the system to the upper, middle and lower vertebrae, respectively. The screws 144 and 145; 146 and 147; and 148 and 149 include receiver portions 153 and 154; 155 and 156; and 157 and 158, respectively, that each preferably define a U-shaped channel for receiving a flexible tether 159. Flexible tether 159 is preferably a flexible rope, cable or rod. It should be understood that other types and configurations of flexible tethering systems are contemplated as within the scope of the present invention. For use in the present invention, the tether 159 is preferably flexible rather than being rigid as might be required for applications in which a fixed relationship between components is desired.

It is known that there are differences among patients in a given population with regard to spinal component spacing, size, shape, configuration, etc., for example, differences in the size of a particular vertebra (e.g., C7) or the spacing between particular adjacent vertebrae (e.g., C4-C5). Such differences are also seen between or among like spinal components (e.g., vertebrae, facet joints, etc.) in a given patient. Accordingly, the prosthetic components described herein can exhibit a variety of suitable shapes and sizes to account for these differences. In certain aspects, the invention provides a line of medical products including one or more prosthetic components of the invention in a sealed package. When a plurality of components are included, the components can each be of substantially the same size and shape, or, alternatively, can vary with respect to size and shape.

In some forms of the invention, medical products are provided that include one or more prosthetic components such as any of those described herein enclosed within sterile medical packaging. Illustratively, such a medical product can have packaging including a backing layer and a front film layer that are joined by a boundary of pressure-adhesive as is conventional in medical packaging, wherein the contents of the packaging are sealed between the backing layer and front film layer. Sterilization of such a medical product may be achieved, for example, by irradiation, ethylene oxide gas, or any other suitable sterilization technique, and the materials and other properties of the medical packaging will be selected accordingly.

Additionally, the package can include indicia to communicate the contents of the package to a person, machine, computer, and/or electronic device. Such indicia may include information such as but not limited to the dimensions of contents, the materials used to form the contents, etc. In certain embodiments, the prosthetic components are packaged for sale with instructions for use. For example, in certain preferred embodiments, a medical product includes at least one prosthetic component sealed within a sterile package, wherein the packaging can have visible indicia identifying the at least one prosthetic component as a facet joint repair device, and/or can contain or otherwise be associated with printed materials identifying the contents as a facet joint repair device or other suitable spinal repair device and including information concerning its use as such a device. The packaging could also include visible indicia relating to the dimension of the at least one prosthetic component, and/or relating to the area of the spine for which the at least one component is configured.

Also to account for differences seen among patients in a given population (or within an individual patient) with regard to spinal component spacing, size, shape, configuration, etc., certain embodiments of the present invention provide prosthetic components having an adjustability to allow the surgeon to adapt the components to suit a particular surgical application or patient, and in this regard, these components can be considered "customizable." In one aspect, the invention provides a prosthetic component for repairing adjacent facet joints on the same side of a spinal column, wherein the component is adjustable in a generally vertical direction to allow the surgeon to select a suitable device height for the particular portion of the spine being treated.

Illustratively, an inventive prosthesis can include a mounting portion extending between a superior portion and an inferior portion, wherein the mounting portion is adapted for connection to a vertebral portion occurring between a first cervical facet joint and a second cervical facet joint, and is configured for adjusting the distance between a point on the superior portion and a point on the inferior portion. Once desirably adjusted, the mounting portion can be fixed, either reversibly or irreversibly, in this position. In some forms, such a mounting portion can be made adjustable by incorporating a screw-type element, a ratcheting system, a slide-and-lock-type element, or any other suitable adjustment means known in the art.

In some forms, an adjustable mounting portion is comprised of two or more mounting members engaged or otherwise suitably associated with one another so as to be adjustable. Illustratively, a first mounting member extending from a superior articulating portion can be adapted to translate along a second mounting member extending from an inferior articulating portion, for example, by having a portion of the first mounting member slidable over the second mounting member or received in the second mounting member. In one aspect, an end of a first mounting member and an end of a second mounting are positioned so that the ends abut one another, and then the ends are fixed together. As well, in embodiments where one or more bone anchor members are used to anchor the prosthesis to the spine, such first and second mounting members may be fixed together in a desirable position independent of the bone anchor member(s), or alternatively, fixing the members together may depend on the bone anchor member(s).

Figure 17:
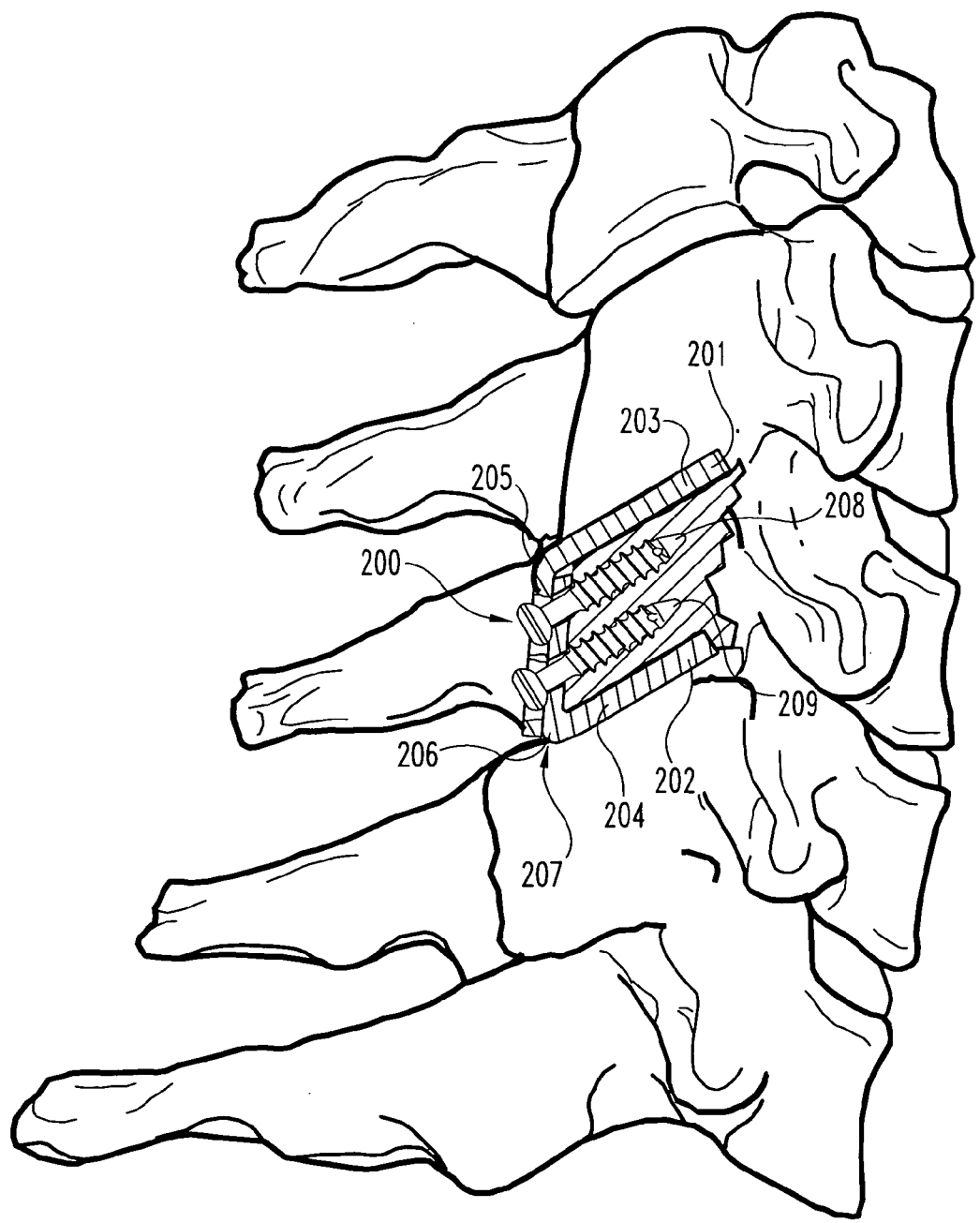
FIG. 17 is a view similar to FIG. 1 showing a further embodiment of the invention.

With reference now to FIG. 17, shown is a prosthetic component 200 comprised of a superior portion 201 and an inferior portion 202. Superior portion 201 is adapted for replacing at least a portion of the articulating surface of a superior articular facet occurring on one side of a cervical vertebra, while inferior portion 202 is adapted for replacing at least a portion of the articulating surface of the inferior articular facet occurring on this same cervical vertebra side. Superior portion 201 and inferior portion 202 include articulation portions 203 and 204, respectively, defining articulating surfaces. Superior portion 201 extends from a first mounting member 205, and inferior portion 202 extends from a second mounting member 206, which together are adapted for connection to the cervical vertebra, e.g., for posterior attachment to the lateral mass 207 of a vertebra via one or more bone anchor members such as bone screws 208 and 209.

Figure 18:
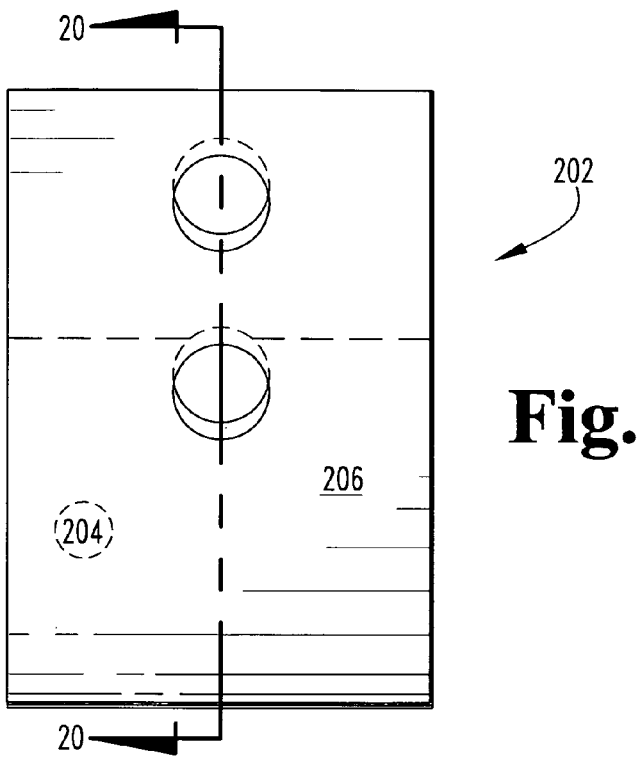
FIG. 18 is a front elevation of an inferior portion and a mounting portion forming part of FIG. 17.
Figure 19:
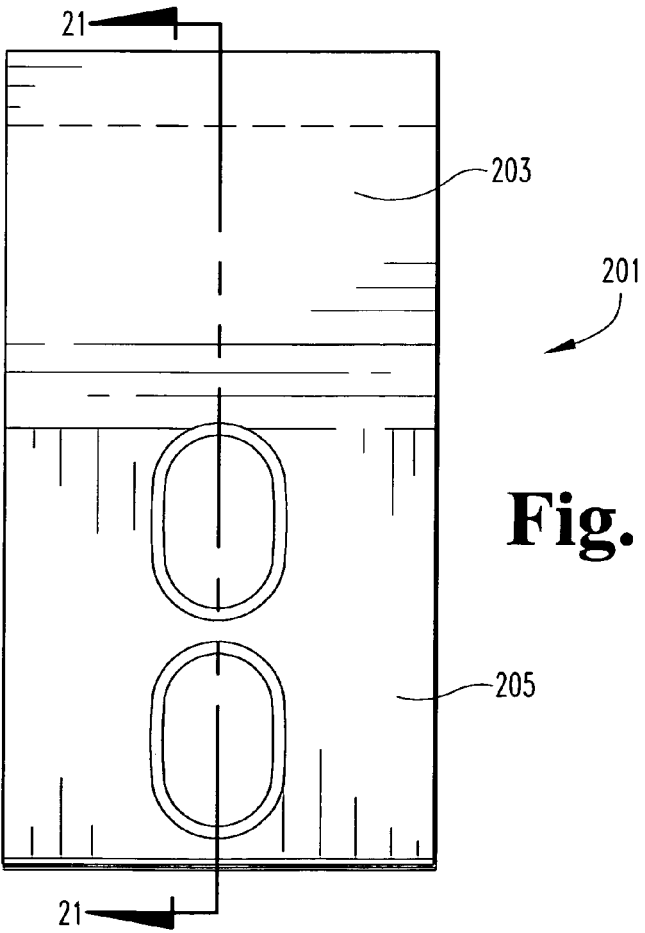
FIG. 19 is a front elevation of a superior portion and a mounting portion forming part of FIG. 17.
Figure 20:
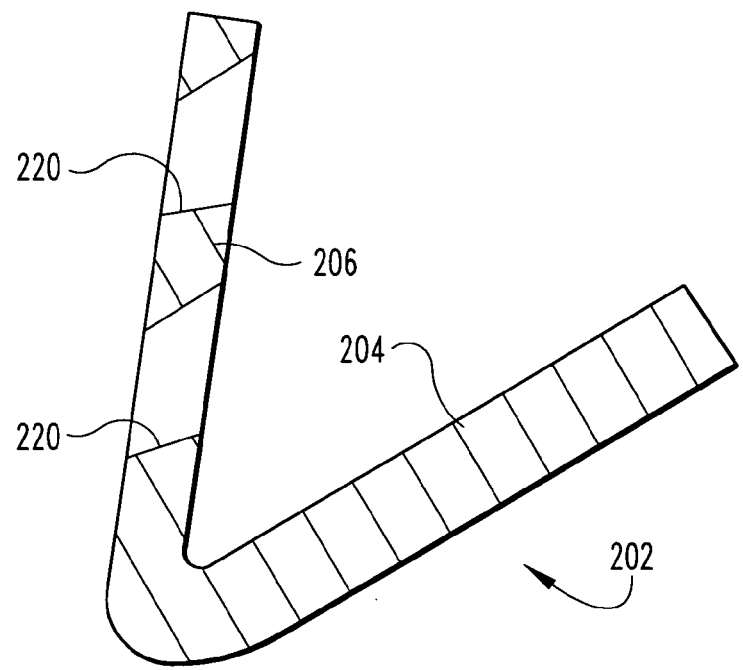
FIG. 20 is a sectional view taken in the direction of the arrows 20-20 in FIG. 18.
Figure 21:
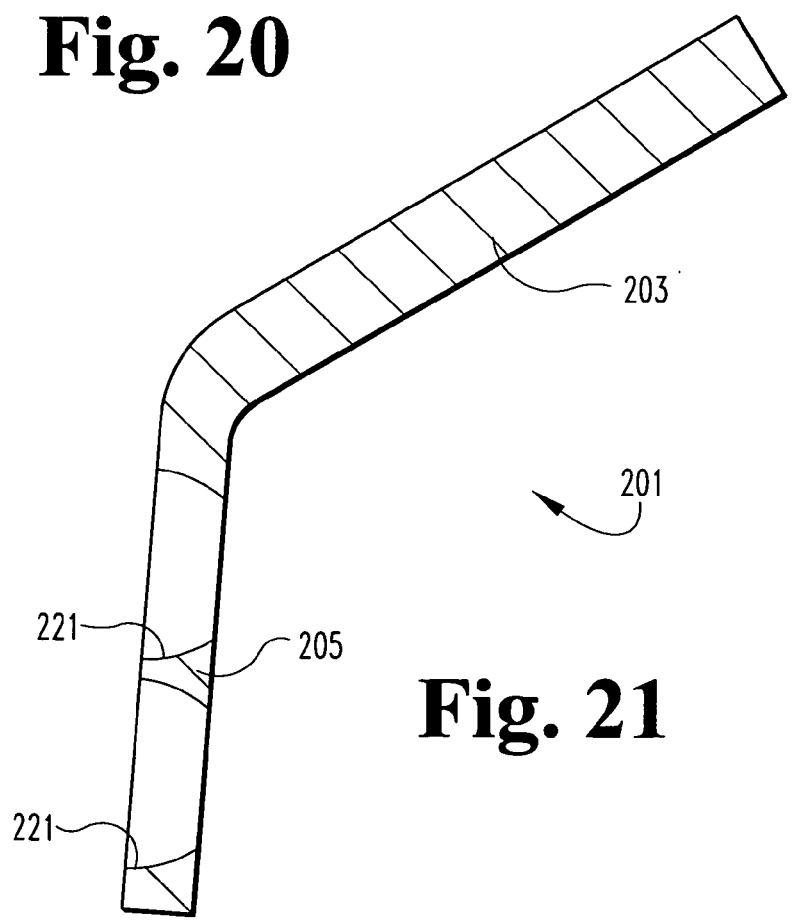
FIG. 21 is a sectional view taken in the direction of the arrows 21-21 in FIG. 19.

FIG. 18 is a front elevation and FIG. 20 is a section showing the configuration of the inferior portion 202. In one specific embodiment, the flat or slightly curvilinear articulation portion 204 and the second mounting member 206 are preferably arranged at an angle of 45° relative to one another. Alternatively, the angular relationship may be about 45°. FIG. 19 is a front elevation and FIG. 21 is a section showing the configuration of the superior component 201. In one specific embodiment, the flat or slightly curvilinear articulation portion 203 and the first mounting member 205 are preferably arranged at an angle of 135° relative to one another. Alternatively, the angular relationship may be about 135°.

Prosthetic component 200 can be arranged as shown in FIG. 17, i.e., with second mounting member 206 positioned between the lateral mass 207 and first mounting member 205. Alternatively, component 200 can be arranged with first mounting member 205 sandwiched between second mounting member 206 and lateral mass 207. In the current embodiment, bone anchor holes 220 are formed in second mounting member 206, while first mounting member 205 has bone anchor slots 221 formed therein. Each of holes 220 are defined by a generally cone-shaped channel formed in second mounting member 206, which allow the surgeon to orient the screws at a variety of angles so as to place the screws in the strongest portions of the bone. Slots 221 allow the surgeon to move the first mounting portion 205 back and forth in a generally vertical direction relative to second mounting portion 206, and thus adjust the "height" of component 200 as desired.

In another aspect, the invention provides a facet joint prosthesis including a superior portion, an inferior portion and a mounting portion, wherein at least one of the superior portion and the inferior portion is translatable along the mounting portion for adjusting the height of the prosthesis, i.e., changing the distance between a point on the superior portion and a point on the inferior portion.

Figure 22:
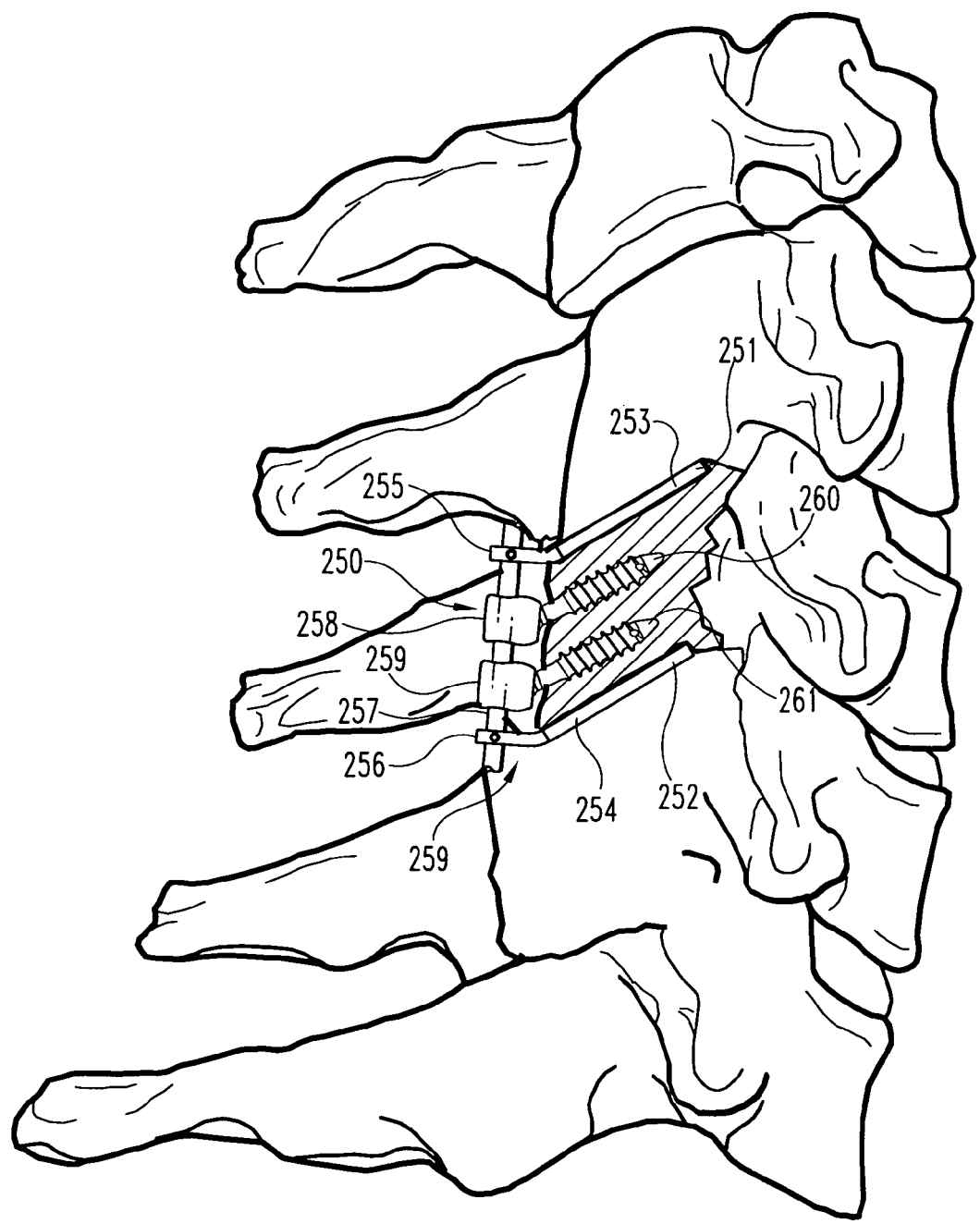
FIG. 22 is a view similar to FIG. 1 showing another embodiment of the invention.

Referring now to FIG. 22, shown is a prosthetic component 250 comprised of a superior portion 251 and an inferior portion 252. Superior portion 251 is adapted for replacing at least a portion of the articulating surface of a superior articular facet occurring on one side of a cervical vertebra, while inferior portion 252 is adapted for replacing at least a portion of the articulating surface of an inferior articular facet occurring on the same side of the cervical vertebra. Superior portion 251 and inferior portion 252 include thin, plate-like articulation portions 253 and 254, respectively, defining articulating surfaces. Superior portion 251 extends from a first mounting member-receiving portion 255, and inferior portion 252 extends from a second mounting member-receiving portion 256, which are both suitably adapted for receiving a mounting rod 257. Rod 257 is preferably rigid or semi-rigid, and is additionally received in bone anchor-receiving portions 258 and 259 of bone anchors 260 and 261, respectively. Each of the mounting member-receiving portions and the bone anchor-receiving portions preferably provide a channel (e.g., a U-shaped or other suitably shaped channel or space) for receiving rod 257 or another suitable mounting member. It will be understood that other superior portion, inferior portion and mounting portion configurations allowing translation of at least one of the superior portion and the inferior portion along the mounting portion are contemplated as within the scope of the present invention. Also, articulation portions 253 and 254 (or any of the other plate-like articulation portions described herein) can have a variety of thicknesses as desired. When an inventive component has more the one articulation portion, the thickness of these potions can vary between or among the portions.

Figure 23:
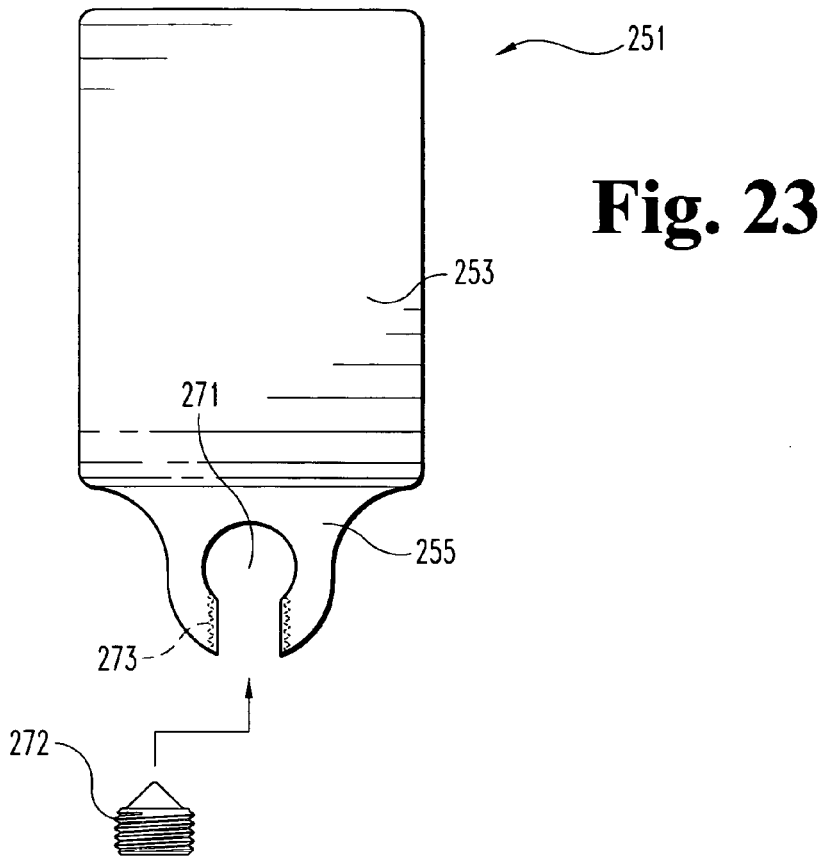
FIG. 23 is a front elevation of a superior portion and a mounting portion forming part of FIG. 22.

FIG. 23 is a front elevation showing the configuration of superior portion 251. In one specific embodiment, the flat or slightly curvilinear articulation portion 253 and the first mounting member-receiving portion 255 are preferably arranged at an angle of 135° relative to one another. Alternatively, the angular relationship may be about 135°. It should be noted that the same devices or ones similar could be used to provide inferior portion 252. First mounting member-receiving portion 255 provides a channel 271 for receiving rod 257. Once rod 257 is desirably positioned in channel 271, the surgeon can insert screw 272 into screw-receiving tract 273, and then tighten screw 272 to suitably contact rod 257 and fix it in place.

In some forms, the invention provides a prosthetic component that includes an articulation portion, a mounting portion, and an adjustable joining portion joining the mounting portion to the articulation portion, wherein the joining portion is configured for adjusting the angle between the mounting portion and the articulation portion. Such a joining portion may be comprised of any suitable device or system for allowing this adjustment including but not limited to a hinge or hinge-like device or a segment formed with a suitable material to enable the surgeon or other user to bend the segment to achieve the desired angle adjustment. Alternatively, the joining portion may be comprised of other suitable one-part and multiple (e.g., two) part devices allowing such angle adjustment, for example, wherein one portion slides over or in part of the other portion to provide the desired angle adjustment, and then is fixed in place (e.g., with a set screw or other suitable locking mechanism).

Any of the prosthetic components described herein having at least one articulation portion and a mounting portion (e.g., including but not limited to the components shown in FIGS. 12, 13 and 17) could be similarly adapted to allow adjustment of the angle between an articulation portion and the mounting portion, for example, from about 40° to about 50° in some components, and from about 130° to about 140° in other components.

Figure 24:
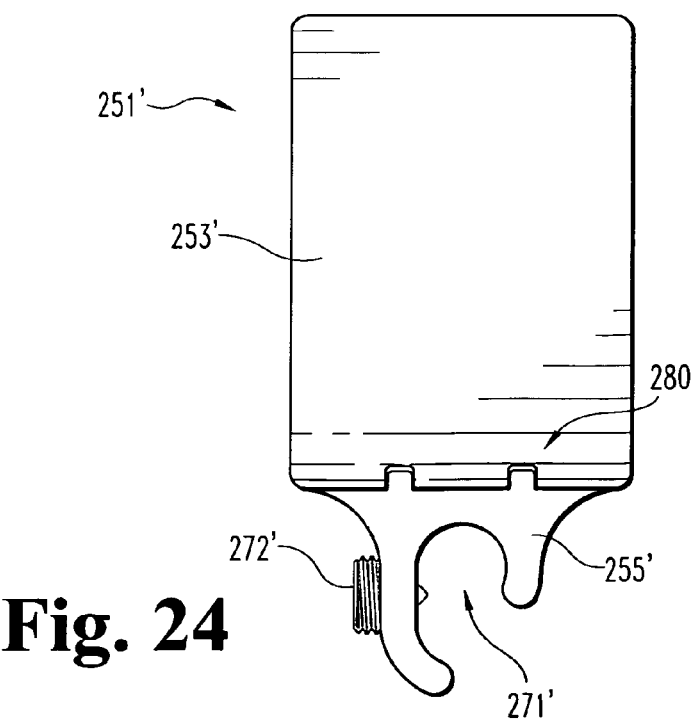
FIG. 24 is a view similar to FIG. 23 showing another embodiment of the invention.

As well, prosthetic components including an articulation portion and a mounting member-receiving portion (e.g., including but not limited to the superior portion 251 shown in FIG. 22) could be similarly adapted to allow adjustment of the angle between the articulation portion and the mounting member-receiving portion. Thus, with reference now to FIG. 24, shown is a front elevation of superior portion 251' which is similar to that shown in FIG. 23 except that superior portion 251' includes a hinged portion 280 allowing adjustment of the angle between articulation portion 253' and first mounting member-receiving portion 255', e.g., from about 130° to about 140°. In one embodiment, hinged portion 280 allows the angle between articulation portion 253' and first mounting member-receiving portion 255' to be adjusted to about 130° to about 140°, and then suitably fixed in place in a manner recognized by one skilled in the art, for example, using an incorporated set screw system. As well, superior portion 251' includes a differently configured first mounting member-receiving portion 255' for receiving rod 257 and fixing it to superior portion 251'.

One method of the present invention for repairing a cervical facet joint of adjacent vertebrae involves providing a superior component having a first substantially flat or slightly curvilinear portion and a mounting portion. An inferior component is provided having a second substantially flat or slightly curvilinear portion and a mounting portion. The articulating surfaces of the natural facet joint are removed only a sufficient amount to allow insertion of the first and second portions therebetween in an overlapping relationship. The first and second portions are then inserted between the facets with the first and second portions in an overlapping relationship. The components are preferably secured to the adjacent vertebrae by attaching the mounting portions to the posterior arches of the adjacent vertebrae.

The step of removing the natural articulating surfaces of the natural facet joint can be accomplished with various surgical instruments or tools. The instrument that is used should be chosen so as to make possible effecting the exact desired dimensions of the joint. The instrument could be an oscillating saw or saws. Also, a high speed burr might be used.

In order to practice this method, preferably a guide or guides is placed into the facet joint. The guide or guides may be a flat spatula-appearing device which is placed into the joint. The guide or guides are cephalad and caudad to the center of the natural facet joint to make room to place the artificial facet joint. The guide is preferably a jig, similar to those used for total knees to cut the total knees or similar to those used in the anterior lumbar spine to cut the end plates. The jig is set up so that either an oscillating saw or a high speed burr is used to make the cuts that allow the placement of the artificial joint. Once the cuts are made, the end plates of the natural facet joint are removed so that the surgeon can look into the area where the cuts are made to make sure there are no osteophytes or any other pieces of bone that are at the tips of the natural facet joint. That is where the nerve is so the surgeon should make sure there are no big bone spurs that are deep so it should be decompressed. Once the cuts have been made preferably the surgeon will place the artificial joint as one piece with the two components married together. The artificial joint will be put in preferably as one piece. It should fit perfectly because by use of the jig to make the cuts there will be exact matching of the dimensions of the facet joint. Preferably it is put in as or similar to a press fit. Then the surgeon places the anchors or screws in to seat the artificial joint preferably with lateral mass screws. In one of the preferred embodiments, there is a tether which provides dynamic stabilization. By using the elastic tether, the facet joint is tensioned perfectly. If the procedure is done with artificial disc replacement, the artificial discs are already placed in front so that has been done first and then the tether is tensioned so that the spine is in the perfect saggittal alignment so that on a lateral x-ray, normal lordosis is achieved and confirmed. Thus, the tether (or soft rod) is used to tension this dynamic stabilizing structure and actually that will allow sliding articulation of the facet joint so that absolutely normal saggittal alignment is obtained.

In order to practice the method shown in FIGS. 11 and 12 wherein only one of the articulating surfaces of the natural facet joint is replaced, the procedure is as follows. A component is provided having a first substantially flat or slightly curvilinear portion and mounting portion. The natural facet surface of a first vertebra is removed only a sufficient amount to allow the insertion of the first portion into overlapping relationship with the natural facet surface of the second vertebra. The first portion is then inserted into overlapping relationship with the natural facet surface of the second vertebra and the component is preferably secured to the first vertebra by attaching the mounting portion to the posterior arch of the first vertebra.

One method of the present invention for repairing and/or replacing articulating surfaces in more than one cervical facet joint, for example, a superior facet articulating surface and an inferior facet articulating surface occurring on the same side of a cervical vertebra, involves providing a single prosthetic component having a superior prosthetic portion, an inferior prosthetic portion and a mounting portion, wherein the superior prosthetic portion and the inferior prosthetic portion each include articulation portions defining articulating surfaces. The natural articulating surfaces of a superior facet and an inferior facet are removed only a sufficient amount to allow insertion of the superior prosthetic portion and the inferior prosthetic portion in the respective facet joints, and then these portions are so inserted. The component is preferably secured to the vertebra by attaching the mounting portion to the posterior arch of the vertebra. Removing the native articulating surfaces of the facet joints, or any portions thereof, and implanting such a prosthesis can be accomplished in any suitable manner, for example, using any of the surgical instruments or tools described above or any other device that would be useful in repairing, replacing or otherwise treating multiple facet joints. Illustratively, a jig such as that described above could be used, or alternatively, a jig or other suitable apparatus useful in the repair of two facet joints occurring on the same side of the cervical spine, could be provided.

Similar methods may be used to implant height-adjustable prostheses such as those shown in FIGS. 17 and 22 within a patient. In implanting such devices, the height may be adjusted before or during the implantation procedure. In some cases, a first component may be secured to the spine before securing a second component to the first component and/or the spine. As well, components allowing adjustment of the angle between an articulating portion and a mounting portion (or other component portion) may be adjusted before or during an implantation procedure.

In order to practice the method shown in FIGS. 14 and 15 wherein two facet joints on the same side of the cervical spine are repaired, the procedure is as follows. A first prosthetic component is provided having a superior prosthetic portion, an inferior prosthetic portion and a mounting portion, wherein the superior prosthetic portion and the inferior prosthetic portion each include substantially flat or slightly curvilinear articulation portions defining articulating surfaces. Also provided are a superior component and an inferior component each having a substantially flat or slightly curvilinear articulation portion, defining an articulating surface, and a mounting flange portion extending transversely from the respective articulation portion. The articulating surfaces of a first facet joint and a second facet joint are removed only a sufficient amount to allow the insertion of the middle component, superior component and inferior component, with the articulating portion of the superior component in an overlapping relationship with the superior portion of the middle component, and the articulating portion of the inferior component in an overlapping relationship with the inferior portion of the middle component, respectively. The three components are then so inserted (individually or otherwise), and preferably secured to the respective vertebrae by attaching the mounting portions to the posterior arches of the respective vertebrae. Again, removing the native articulating surfaces of the facet joints, or any portions thereof, and implanting such a combination of prosthetic components can be accomplished in any suitable manner, for example, using any of the surgical instruments or tools described above or any other device that would be useful in the treatment of multiple facet joints. Additionally, it will be appreciated by those skilled in the art that the individual components described herein can be combined and used in a variety of manners to provide suitable treatment systems. Illustratively, two components such as component 100 could be used in a mating relationship to repair three facet joints occurring on the same side of a spinal column.

It can be appreciated that the prostheses and procedures described herein make possible improved treatment of the spine. For example, these procedures may be used in combination with disc replacement in order to restore spine alignment. Further in the case of a fracture, the concepts taught herein may be used to repair a facet joint by replacing only one of the natural facet surfaces.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed:

1. A prosthesis for the repair of a first cervical facet joint and a second cervical facet joint occurring on a first side of a spinal column, the first cervical facet joint having a superior facet articulating surface and an inferior facet articulating surface, the second cervical facet joint having a superior facet articulating surface and an inferior facet articulating surface, the prosthesis comprising:

a first prosthetic component, comprising:

a first prosthetic component superior portion adapted for replacing at least a portion of the articulating surface of the first cervical facet joint superior facet;

a first prosthetic component inferior portion adapted for replacing at least a portion of the articulating surface of the second cervical facet joint inferior facet; and a first prosthetic component mounting portion adapted for connection to a vertebral portion occurring between the first cervical facet joint and the second cervical facet joint, wherein the first prosthetic component superior portion is joined to the mounting portion at an angle of about 135°.

2. The prosthesis of claim 1, further comprising:
a third prosthetic component, comprising:
a third prosthetic component superior portion adapted for replacing at least a portion of the articulating surface of the second cervical facet joint superior facet; and
a third prosthetic component mounting portion adapted for connection to a vertebral portion occurring below the second cervical facet joint.

3. The prosthesis of claim 2, wherein the third prosthetic component superior portion is joined to the third prosthetic component mounting portion at an angle of about 135°.

4. The prosthesis of claim 1, further comprising a bone anchor member for attaching the first prosthetic component to a vertebral portion occurring between the first cervical facet joint and the second cervical facet joint.

5. The prosthesis of claim 4, wherein the bone anchor member is a screw.

6. The prosthesis of claim 4, wherein the bone anchor member can be selectively oriented in at least two positions relative to the first prosthetic component when attaching the first prosthetic component to the vertebral portion.

7. The prosthesis of claim 1, wherein the first prosthetic component mounting portion comprises a mounting member extending between the first prosthetic component superior portion and the first prosthetic component inferior portion.

8. The prosthesis of claim 1, wherein the first prosthetic component mounting portion comprises:
a first mounting member extending from the first prosthetic component superior portion; and
a second mounting member extending from the first prosthetic component inferior portion.

9. The prosthesis of claim 8, wherein the first mounting member is connected to the second mounting member.

10. The prosthesis of claim 8, wherein the first mounting member overlaps the second mounting member.

11. The prosthesis of claim 8, wherein the first mounting member has a portion received in the second mounting member.

12. The prosthesis of claim 8, wherein at least one of the first prosthetic component superior portion and the first prosthetic component inferior portion are translatable along the first prosthetic component mounting portion for adjusting the distance between a point on the superior portion and a point on the inferior portion.

13. The prosthesis of claim 1, further comprising:
a second prosthetic component, comprising:
a second prosthetic component inferior portion adapted for replacing at least a portion of the articulating surface of the first cervical facet joint inferior facet; and
a second prosthetic component mounting portion adapted for connection to a vertebral portion occurring above the first cervical facet joint.

14. The prosthesis of claim 13, wherein the second prosthetic component inferior portion is joined to the second prosthetic component mounting portion at an angle of about 45°.

15. The prosthesis of claim 13, further comprising:
a third prosthetic component, comprising:
a third prosthetic component superior portion adapted for replacing at least a portion of the articulating surface of the second cervical facet joint superior facet; and
a third prosthetic component mounting portion adapted for connection to a vertebral portion occurring below the second cervical facet joint.

16. The prosthesis of claim 15, further comprising:
a first bone anchor member for attaching the first prosthetic component to a vertebral portion occurring between the first cervical facet joint and the second cervical facet joint;
a second bone anchor member for attaching the second prosthetic component to a vertebral portion occurring above the first cervical facet joint;
a third bone anchor member for attaching the third prosthetic component to a vertebral portion occurring below the second cervical facet joint; and
a flexible tethering system connecting the first bone anchor member, the second bone anchor member, and the third bone anchor member.

17. The prosthesis of claim 16, wherein the flexible tethering system comprises a flexible elongated member secured to the first bone anchor member, the second bone anchor member, and the third bone anchor member.

18. A prosthesis for the repair of a first cervical facet joint and a second cervical facet joint occurring on a first side of a spinal column, the first cervical facet joint having a superior facet articulating surface and an inferior facet articulating surface, the second cervical facet joint having a superior facet articulating surface and an inferior facet articulating surface, the prosthesis comprising:
a first prosthetic component, comprising:
a first prosthetic component superior portion adapted for replacing at least a portion of the articulating surface of the first cervical facet joint superior facet;
a first prosthetic component inferior portion adapted for replacing at least a portion of the articulating surface of the second cervical facet joint inferior facet; and
a first prosthetic component mounting portion adapted for connection to a vertebral portion occurring between the first cervical facet joint and the second cervical facet joint,
wherein the first prosthetic component inferior portion is joined to the mounting portion at an angle of about 45°.

19. The prosthesis of claim 18, wherein the first prosthetic component superior portion is joined to the mounting portion at an angle of about 135°.

* * * * *